(12) United States Patent
Arora et al.

(10) Patent No.: US 7,834,038 B2
(45) Date of Patent: Nov. 16, 2010

(54) METHODS FOR PREPARING NONPEPTIDIC OLIGOMERS FROM AMINO ACIDS

(75) Inventors: Paramjit S. Arora, White Plains, NY (US); Nicholas G. Angelo, Tuckahoe, NY (US)

(73) Assignee: New York University, New York, NY (US)

( * ) Notice: Subject to any disclaimer, the term of this patent is extended or adjusted under 35 U.S.C. 154(b) by 708 days.

(21) Appl. No.: 11/595,383

(22) Filed: Nov. 9, 2006

(65) Prior Publication Data

US 2007/0105917 A1    May 10, 2007

Related U.S. Application Data

(60) Provisional application No. 60/734,953, filed on Nov. 9, 2005.

(51) Int. Cl.
*A61K 31/41* (2006.01)
*C07D 249/00* (2006.01)
(52) U.S. Cl. ........................ 514/359; 548/255
(58) Field of Classification Search ................ 514/359; 548/255
See application file for complete search history.

(56) References Cited

U.S. PATENT DOCUMENTS

| 5,877,278 A | 3/1999 | Zuckermann et al. |
| 6,060,585 A | 5/2000 | Gellman et al. |
| 6,613,876 B1 | 9/2003 | Gellman et al. |
| 6,617,425 B1 | 9/2003 | Seebach |
| 6,710,186 B2 | 3/2004 | Gellman et al. |
| 6,727,368 B1 | 4/2004 | Gellman et al. |

FOREIGN PATENT DOCUMENTS

| WO | WO 2005/007675 A2 * | 1/2005 |
| WO | WO2005007675 A2 * | 1/2005 |

OTHER PUBLICATIONS

Amino acid sidechain chart, University of Rochester, 1 webpage, 2009.*

* cited by examiner

*Primary Examiner*—Susannah Chung
(74) *Attorney, Agent, or Firm*—Nixon Peabody LLP

(57) ABSTRACT

The present invention relates to nonpeptidic oligomers. Methods for preparing nonpeptidic oligomers from amino acids by replacing the amide bond with heterocyclic rings are also disclosed.

13 Claims, 25 Drawing Sheets

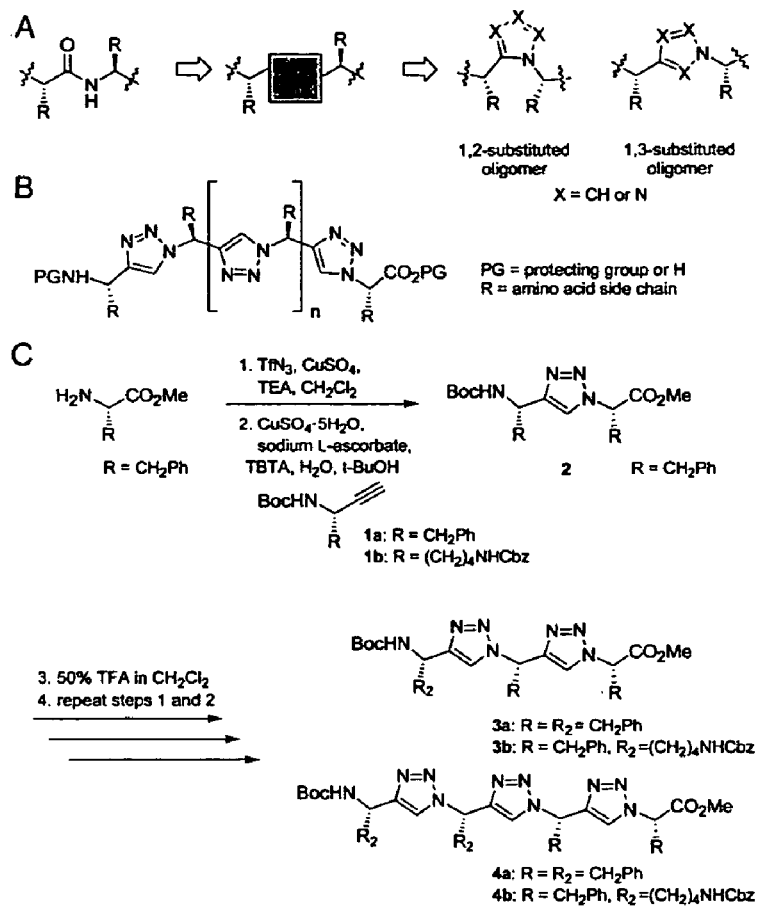
Figures 1A–C
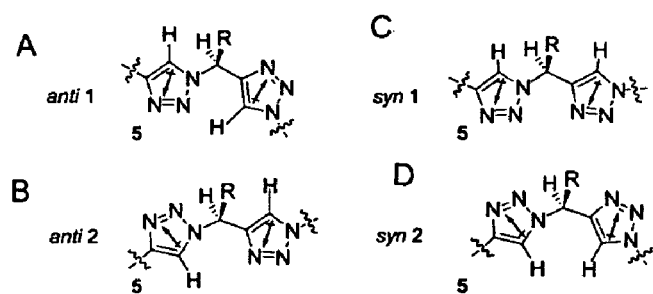
Figures 2A–D

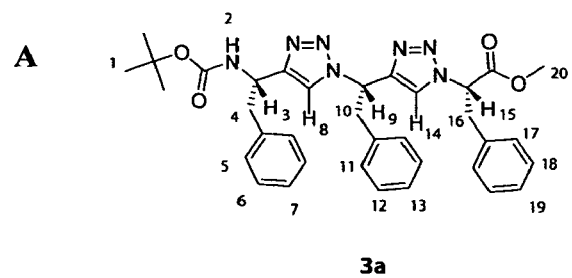
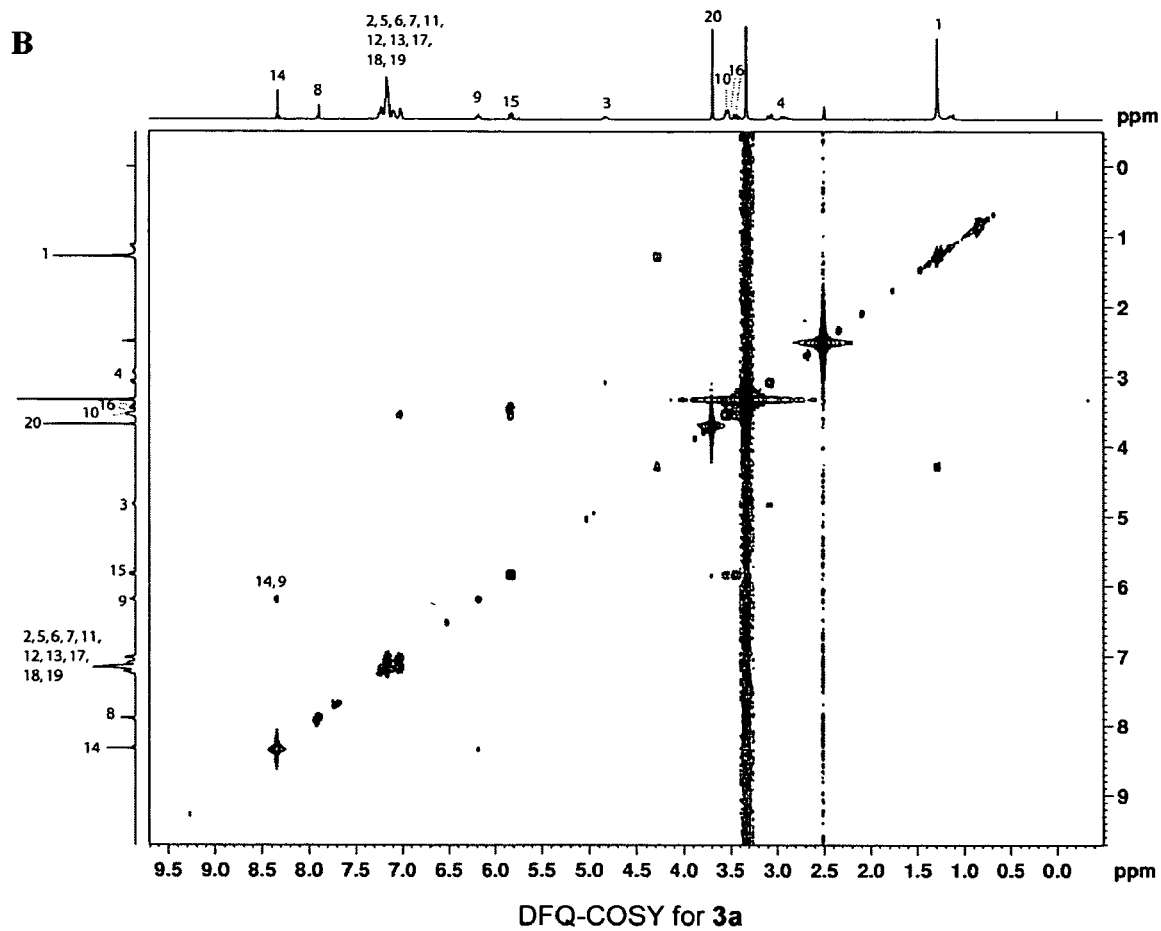
Figures 3A–B

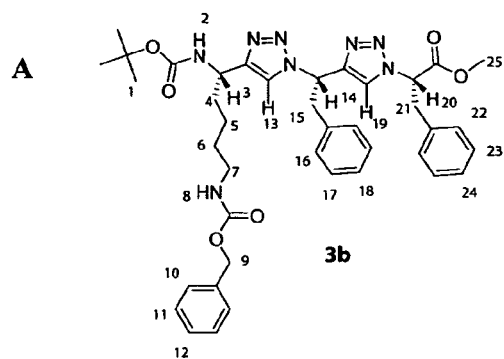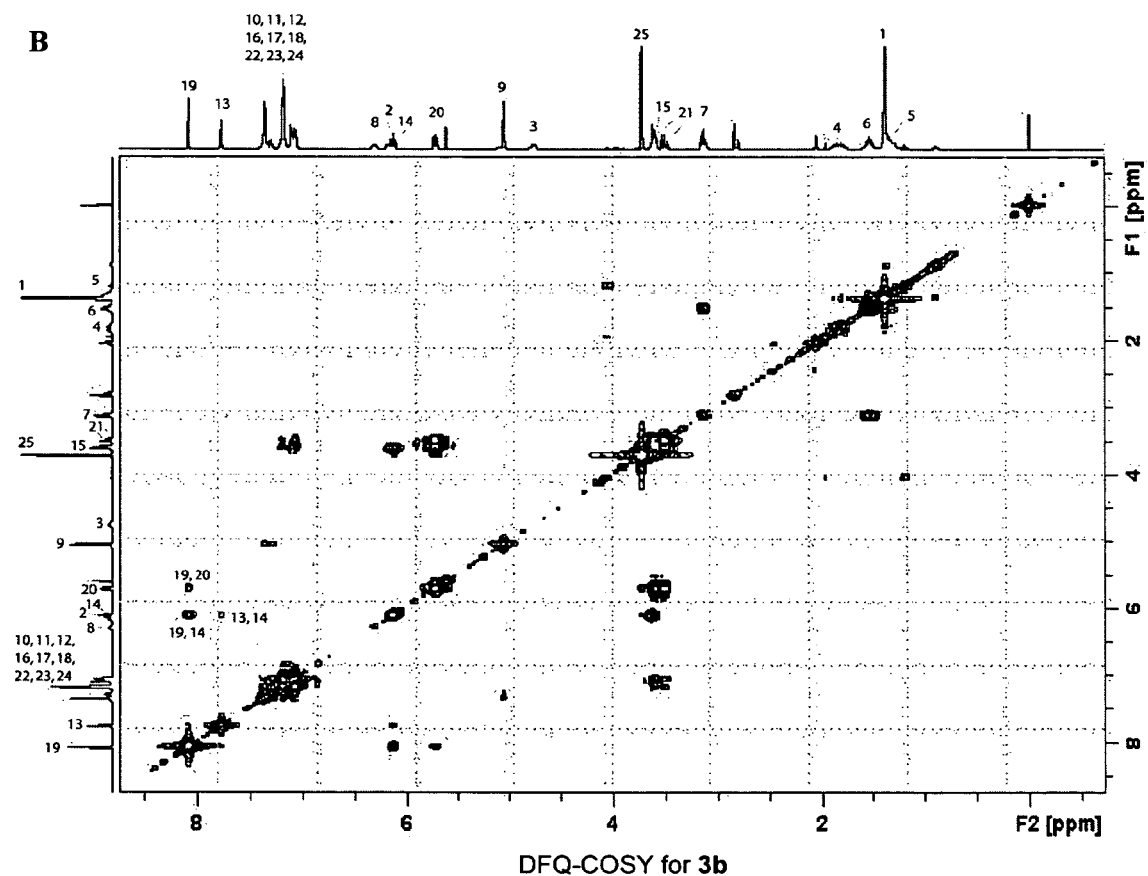
Figures 8A–B

A 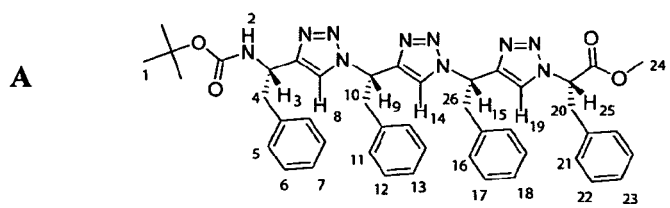
4a
B 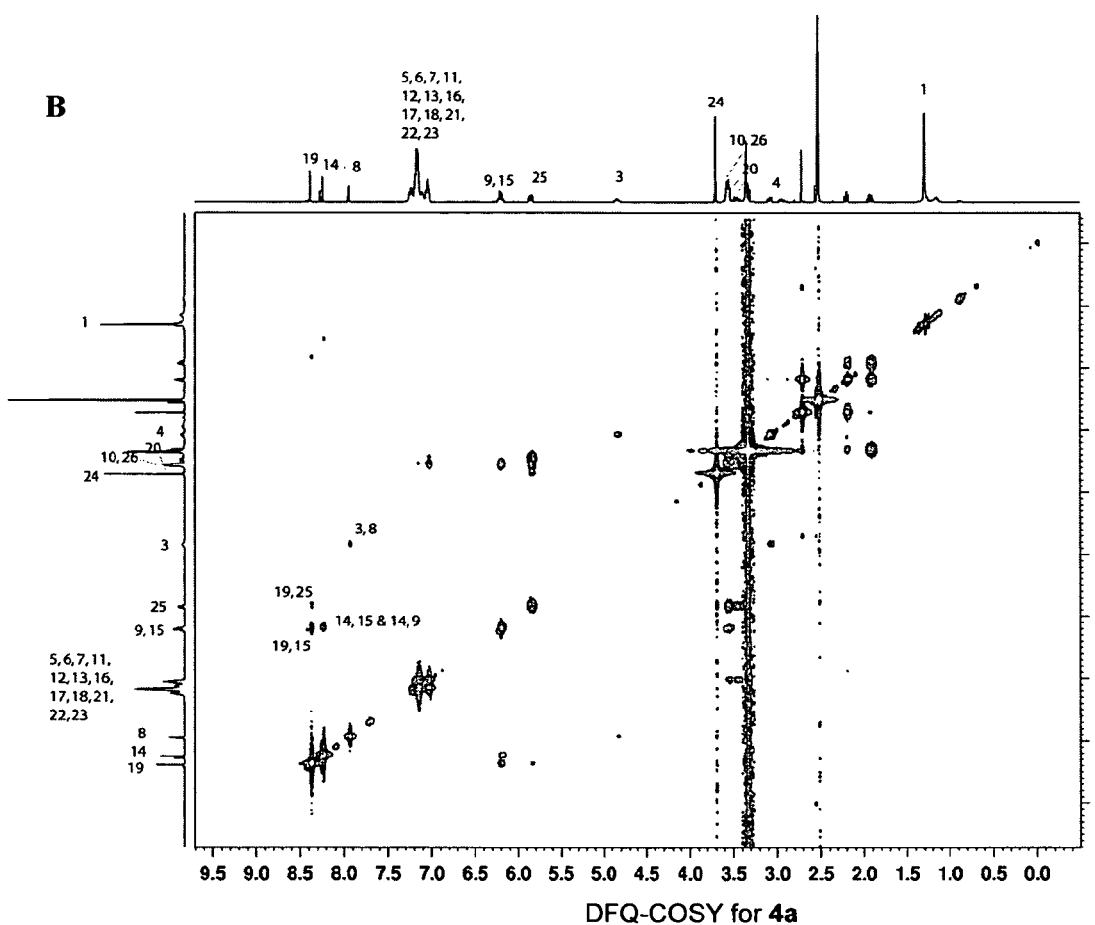
DFQ-COSY for 4a
Figures 13A–B

Figures 18A–B

A 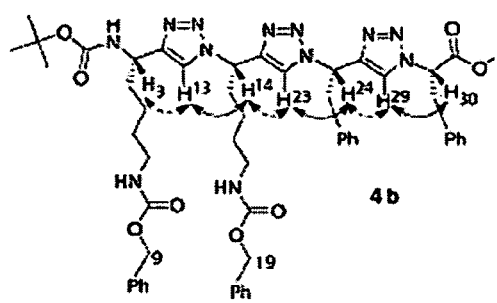
B 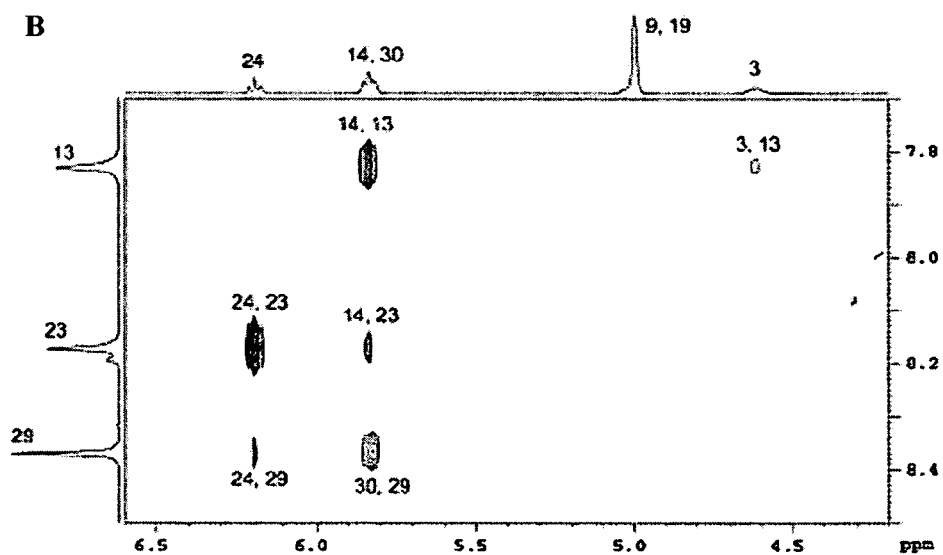
Figures 23A–B

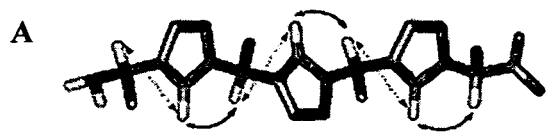
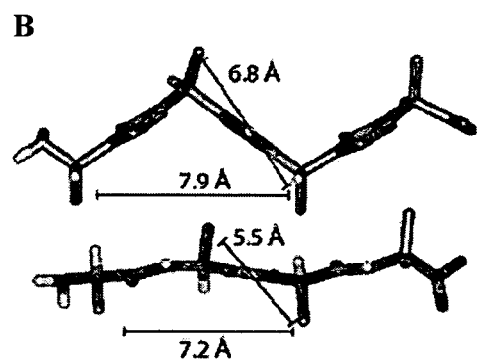
Figures 24A–B
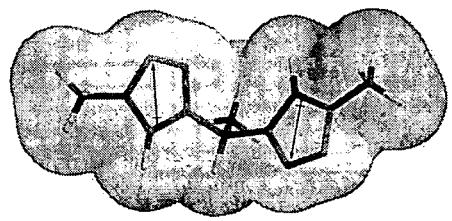
Figure 25
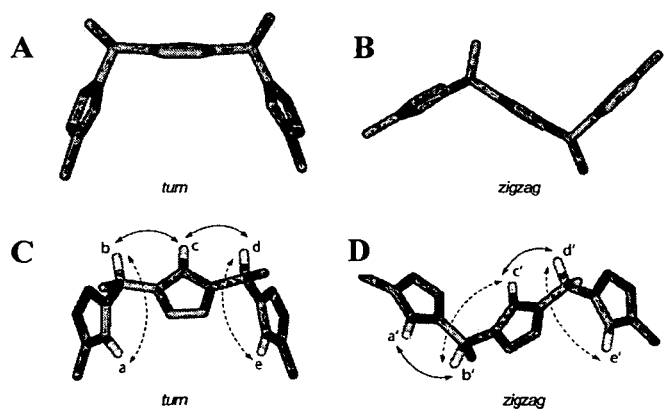
Figures 26A–D

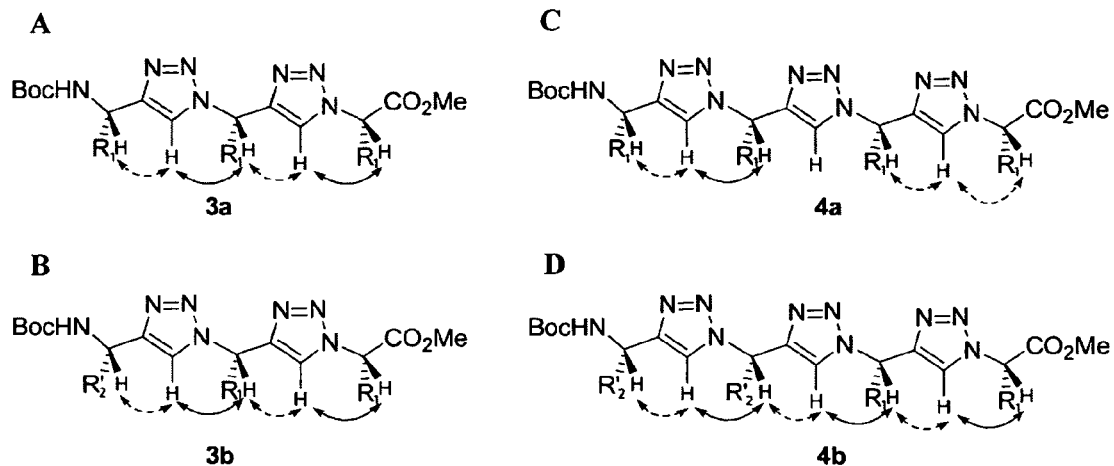
Figures 27A–D
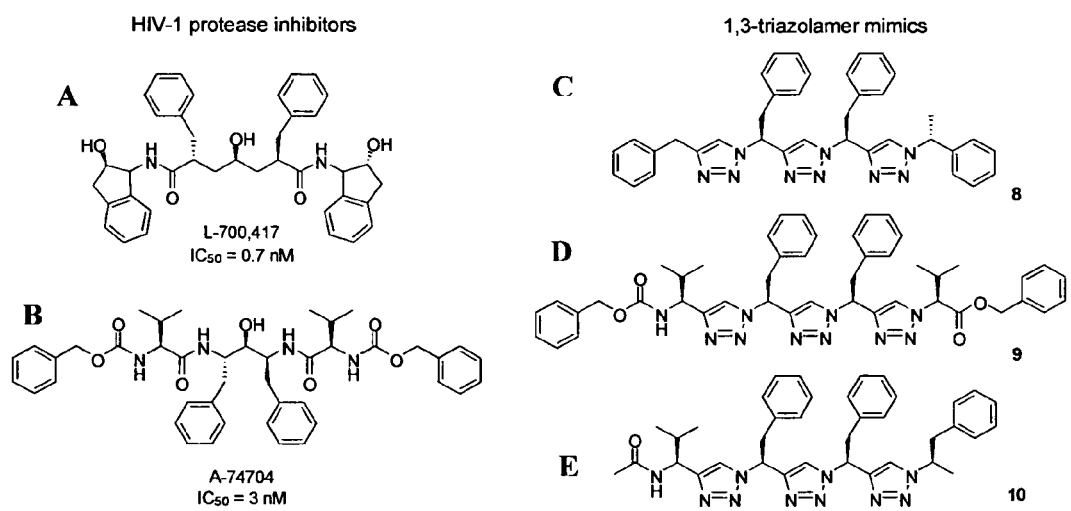
Figures 28A–E

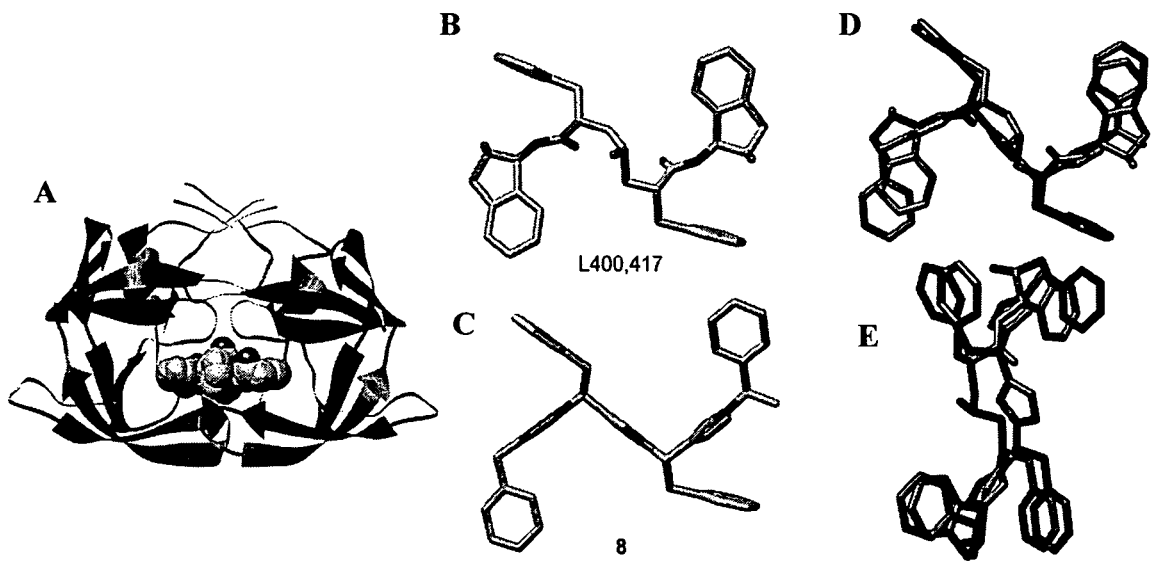
Figures 29A–E
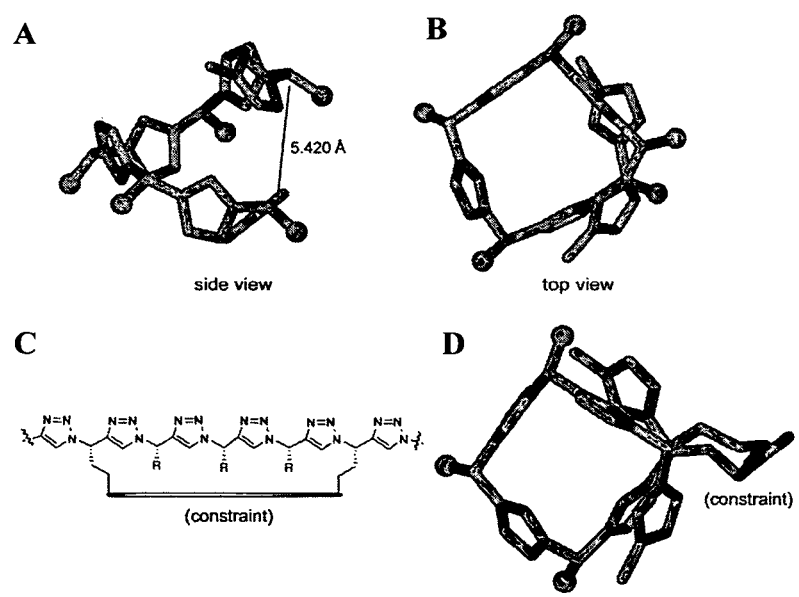
Figures 30A–D

METHODS FOR PREPARING NONPEPTIDIC OLIGOMERS FROM AMINO ACIDS

This application claims the benefit of U.S. Provisional Patent Application Ser. No. 60/734,953, filed Nov. 9, 2005, which is hereby incorporated by reference in its entirety.

FIELD OF THE INVENTION

This invention is directed generally to nonpeptidic oligomers, and methods for preparing nonpeptidic oligomers from amino acids.

BACKGROUND OF THE INVENTION

The intrinsic instability of peptides limits their potential as reagents in molecular biology and drug discovery. Nonpeptidic scaffolds that adopt well-defined conformations and display protein-like side chains would be invaluable alternatives to peptides (Yin & Hamilton, Angew. Chem. Int. Ed. 44:4130-4163 (2005); Gellman, Acc. Chem. Res. 31:173-180 (1998)). Biomimetic oligomers (Gellman, Acc. Chem. Res. 31:173-180 (1998); Sanford et al., Eur. J Biochem. 271:1416-1425 (2004); Hill et al., Chem. Rev. 101:3893-4011 (2001); Barron & Zuckermann, Curr. Opin. Chem. Biol. 3:681-687 (1999); Stigers et al., Curr. Opin. Chem. Biol. 3:714-723 (1999)), such as β-peptides (Cheng et al., Chem. Rev. 101: 3219-3232 (2001); Seebach & Matthews, Chem. Commun. 2015-2022 (1997)), have been intensively studied because they possess a high propensity to adopt defined secondary structures and resist degradation by proteolytic enzymes. These oligomers also retain perhaps the most important asset offered by peptides, namely access to a diverse set of side chain functional groups needed for molecular recognition and catalysis. Several nonpeptidic oligomers composed of carbamates, sulfonamides, ureas, hydrazino acids, aminoxy acids, anthranilamides, oligophenylacetylenes, and pyrrolinones, among others, have been described (U.S. Patent Application Publication No. US 2004/0116654 A1 to Gellman et al.; Gellman, Acc. Chem. Res. 31:173-180 (1998); Sanford et al., Eur. J. Biochem. 271:1416-1425 (2004); Hill et al., Chem. Rev. 101:3893-4011 (2001); Barron & Zuckermann, Curr. Opin. Chem. Biol. 3:681-687 (1999); Stigers et al., Curr. Opin. Chem. Biol. 3:714-723 (1999)). However, some of these oligomers lack peptide main chirality or amino acid side chains, thus limiting their ability to be used as peptide mimics. Thus, there remains a need for identifying a general method for the synthesis of distinctly folded, nonpeptidic oligomers in which the amide bond is replaced by aromatic rings yet the chiral main-chain and amino acid side chains are maintained.

The present invention is directed to overcoming these and other deficiencies in the art.

SUMMARY OF THE INVENTION

One aspect of the present invention relates to a method of preparing a compound of Formula I:

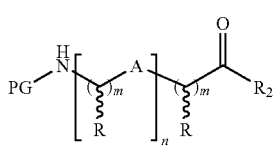

where each "A" moiety is independently a moiety of formula

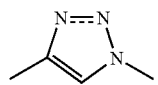

where ---- is a single or double bond;
PG is a protecting group; each R is independently an amino acid side chain;
$R_2$ is $OR_3$ or $N(R_3)_2$; $R_3$ is hydrogen, an alkyl group, an aryl group, or a protecting group; ~~~ is a single bond of undefined stereochemistry; m is independently 1 or 2; and n is any number greater than 1. This method involves providing a compound of Formula II:

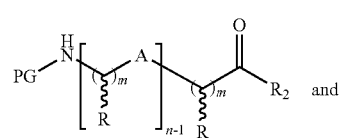

providing a compound of Formula III:

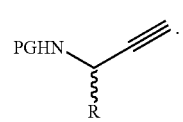

The compound of Formula II is converted with an azide-producing compound and the compound of Formula III to produce the compound of Formula I.

Another aspect of the present invention relates to an oligomer of Formula I.

The methods of the present invention teach how to increase the number of defined backbone conformations possible from amino acids and introduce "druglike" character into these oligomers by swapping the amide bond with aromatic rings and by projecting the attached main-chains at different angles from a given ring (Hirschmann, Angew. Chem. Int. Ed. Engl. 30:1278-1301 (1991); Smith et al., Bioorg. Med. Chem. 7:9-22 (1999); Smith et al., J. Med. Chem. 37:215-218 (1994), which are hereby incorporated by reference in their entirety), as illustrated in FIG. 1A.

The oligomers disclosed here are a new class of distinctly folded, nonpeptidic oligomers in which the amide bond is replaced by aromatic rings yet the chiral main-chain and amino acid side chains are maintained, as shown in FIGS. 1A-1B.

The oligomers of the present invention potentially afford specific conformations featuring a diverse set of side chains without the limitations imposed by the secondary amide bond (Hirschmann, Angew. Chem. Int. Ed. Engl. 30:1278-1301 (1991), which is hereby incorporated by reference in its entirety). The methods of the present invention provide ways to introduce drug-like functionality into the nonpeptidic oligomers produced thereby. By exchanging the amide bond with heteroaromatic rings that often form the basis of drug molecules, biomimetic oligomers with improved pharmacological profiles (for example, that display improved cellular uptake) can be produced. The oligomers can be produced from any amino acids, and can be organized into non-natural peptides that, because the amide bond is replaced by heterocyclic rings, are resistant to proteolytic degradation. The oligomers of the present invention can also adopt stable structural organizations, even at very short lengths (e.g., 8 subunits), at which lengths amide-bond-containing peptides would not naturally adopt a stable conformation.

BRIEF DESCRIPTION OF THE DRAWINGS

FIGS. A-C are schematic diagrams illustrating the development of nonpeptidic foldamers by replacement of the amide bond with triazole rings.

FIG. 1A illustrates the general scheme. FIG. 1B illustrates a 1,3-substituted triazolamer. FIG. 1C illustrates the synthesis of the triazole oligomers from amino acids.

FIGS. 2A-D are schematic diagrams of conformations adopted by triazole dimer 5 (see Example 9). The syn (FIGS. 2C-D) and anti (FIGS. 2A-B) conformations are defined by the dipole-dipole interactions between adjacent triazole rings. The anti conformations are calculated to be roughly 4 Kcal/mol lower in energy than the syn conformations. Molecular mechanics studies were performed with Macromodel (MMFF force field in chloroform) and ab initio calculations were conducted with the Gaussian 03 program package (DFT B3LYP method at 6-31G* level).

FIGS. 3A-B are a schematic diagram of triazolamer 3a (FIG. 3A) and an image of its DFQ-COSY spectrum (FIG. 3B).

FIG. 4 is an image of the TOCSY spectrum for triazolamer 3a.

FIG. 5 is an image of the ROESY spectrum for triazolamer 3a.

FIG. 6 is an image of the $^1$H NMR spectrum for triazolamer 3a.

FIG. 7 is an image of the $^{13}$C NMR spectrum for triazolamer 3a.

FIGS. 8A-B are a schematic diagram of triazolamer 3b (FIG. 8A) and an image of its DFQ-COSY spectrum (FIG. 8B).

FIGS. 13A-B are a schematic diagram of triazolamer 4a (FIG. 13A) and an image of its DFQ-COSY spectrum (FIG. 13B).

FIG. 14 is an image of the TOCSY spectrum for triazolamer 4a.

FIG. 15 is an image of the ROESY spectrum for triazolamer 4a.

FIG. 16 is an image of the $^1$H NMR spectrum for triazolamer 4a.

FIG. 17 is an image of the $^{13}$C NMR spectrum for triazolamer 4a.

FIGS. 23A-B are a schematic diagram of triazolamer 4b (FIG. 23A) and a cross-section of its ROESY spectra (FIG. 23B) (in DMSO-$d_6$) displaying crosspeaks between the aromatic and the $C_\alpha$ protons.

FIGS. 24A-B are illustrations of triazolamer conformations of triazolamer 4b. FIG. 24A shows the predominant triazolamer conformation revealed by ROESY experiments. Solid and dashed lines indicate observed strong and weak NOE crosspeaks, respectively. FIG. 24B shows a comparison of triazolamer 4b in a zigzag conformation (top) to a peptide β-strand (tetraalanine) (bottom). The triazolamer mimics a peptide β-strand with similar axial distances between the i and i+2 side chains. For clarity, side chains are depicted as methyl groups.

FIG. 25 is a schematic drawing illustrating the dipole-dipole interactions between adjacent triazole rings. Arrows depict dipole direction within individual triazole rings. For clarity, side chains are depicted as methyl groups.

FIGS. 26A-D are schematic drawings of tetramer 4. Tetramer 4 can adopt two distinct backbone conformations, labeled turn (FIG. 26A) and zigzag (FIG. 26B). The predicted ROESY crosspeaks for the two conformations are shown in FIG. 26C (turn) and FIG. 26D (zigzag). Patterns and intensities of ROESY crosspeaks are expected to readily reveal the major conformation in solution. Solid and dashed lines indicate (predicted) strong and weak NOE crosspeaks, respectively. For clarity, side chains are depicted as methyl groups.

FIGS. 27A-D are schematic diagrams of the conformations of triazolamers 3a (FIG. 27A), 3b (FIG. 27B), 4a (FIG. 27C), and 4b (FIG. 27D), based on the results of the ROESY experiments performed in DMSO-$d_6$ or acetone-$d_6$. Overlapping NMR signals precluded complete assignment for triazolamer 4a. Solid and dashed lines indicate strong and weak NOE crosspeaks, respectively. $R_1$ is $CH_2Ph$; $R_2$ is $(CH_2)_4NHCbz$.

FIGS. 28A-E are schematic drawings of two potent HIV-1 inhibitors (FIGS. 28A-B) and their triazolamer mimics (FIGS. 28C-E).

FIGS. 29A-E are schematic diagrams showing (a) the structure of L400,417 in complex with an HIV-1 protease (Protein Data Bank ID: 4PHV) (FIG. 29A), (b) the conformation of L400,417 in the complex (FIG. 29B), (c) triazolamer 8 in a zigzag conformation (FIG. 29C), and (d) the superimposition of L400,417 and triazolamer 8 showing similar positioning of their side chains and backbone (two views) (FIGS. 29D-E).

FIGS. 30A-D are schematic drawings of constrained oligomers. FIGS. 30A-B show two views of the lowest energy (MMFF force field in chloroform) helical structure arising from 1,3-triazole rings (see FIGS. 26A-B). FIG. 30C shows a pentamer constrained to lock the triazolamer in a helical conformation as shown in FIGS. 30A-B. Modeling suggests that a ornithine-glutamic acid lactam bridge would be effective in producing a stable single helical turn structure (FIG. 30D). For clarity, side chains are depicted as methyl groups.

DETAILED DESCRIPTION OF THE INVENTION

Figure 4:
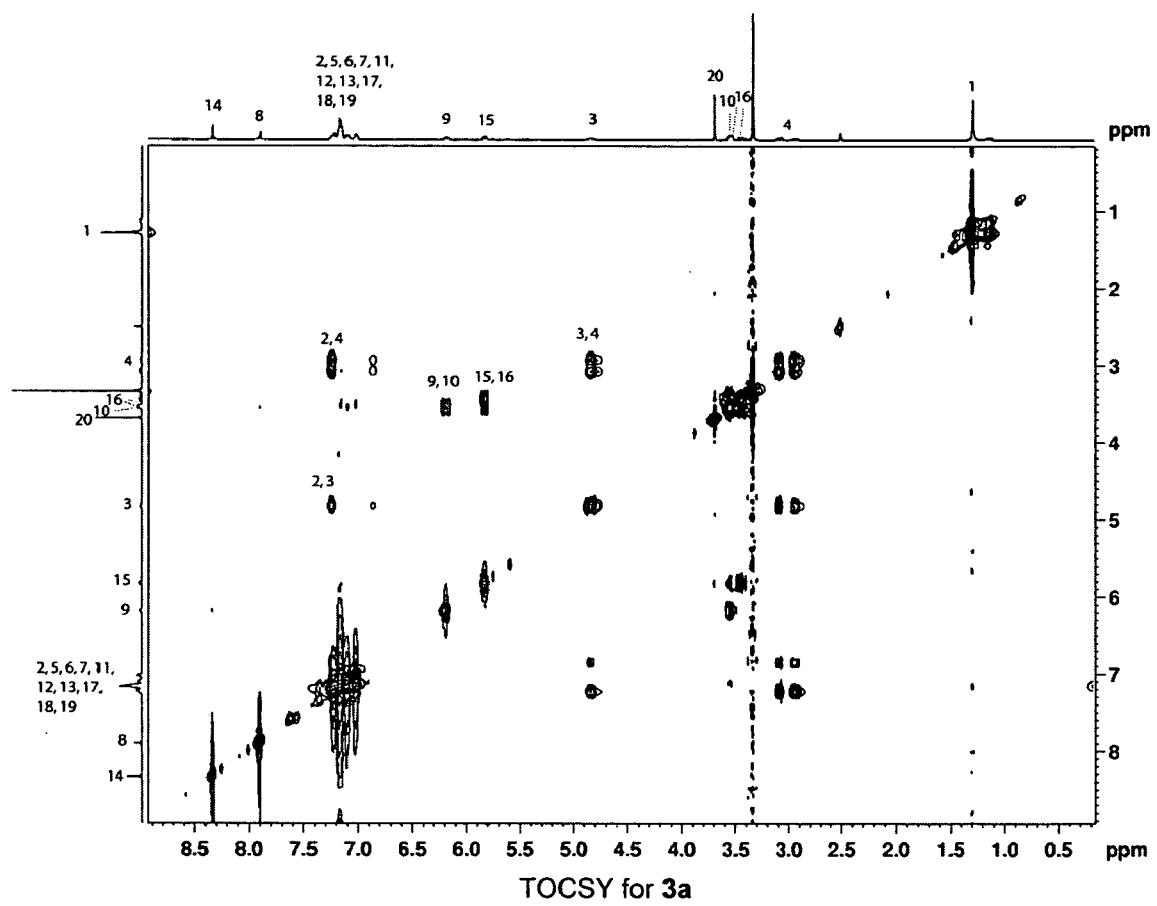

One aspect of the present invention relates to a method of preparing a compound of Formula I:

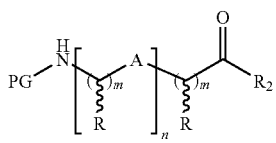

where each "A" moiety is independently a moiety of formula

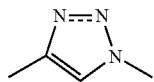

where ----- is a single or double bond;
PG is a protecting group; each R is independently an amino acid side chain; $R_2$ is $OR_3$ or $N(R_3)_2$; $R_3$ is hydrogen, an alkyl group, an aryl group, or a protecting group;
∿∿ is a single bond of undefined stereochemistry; m is independently 1 or 2; and n is any number greater than 1.
This method involves providing a compound of Formula II:

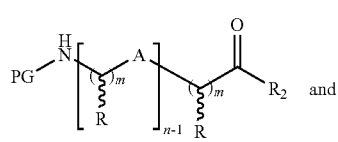

providing a compound of Formula III:

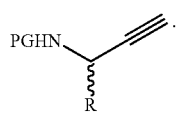

The compound of Formula II is converted with an azide-producing compound and the compound of Formula III to produce the compound of Formula I. In a preferred embodiment, the alkyl group forming $R_3$ is $C_1$ to $C_4$ (e.g., methyl, ethyl, allyl, or t-butyl), while the aryl group forming $R_3$ is $C_6H_5$ (phenyl) or $C_7H_7$ (benzyl).

In previous efforts to produce peptidomimetics (Smith et al., *Bioorg. Med. Chem.* 7:9-22 (1999); Smith et al., *J. Med. Chem.* 37:215-218 (1994); Deng & Taunton, *Org. Lett.* 7:299-301 (2005); Wipf et al., *J. Am. Chem. Soc.* 120:4105-4112 (1998), which are hereby incorporated by reference in their entirety), the amide bond was substituted with heteroaromatic rings to generate peptidomimetics. The present invention extends these methodologies to the synthesis of nonpeptidic oligomers directly from amino acids. Although several ring systems are synthetically accessible, the amide bonds were swapped with triazole rings. This ring system was used because (1) dipeptides bearing both 1,2,3-triazole rings (Brik et al., *ChemBioChem* 6:1167-1169 (2005); Home et al., *J. Am. Chem. Soc.* 126:15366-15367 (2004); Kolb & Sharpless, *Drug Discov. Today* 8:1128-1137 (2003), which are hereby incorporated by reference in their entirety) and 1,2,4-triazole rings (Hitotsuyanagi et al., *J. Org. Chem.* 67:3266-3271 (2002), which is hereby incorporated by reference in its entirety) have been described, and (2) the large dipole moment (~5 Debye) (Bourne et al., *Proc. Nat'l Acad. Sci. USA* 101:1449-1454 (2004), which is hereby incorporated by reference in its entirety) in these rings indicated that defined conformations could be obtained through forces such as dipole-dipole interactions and torsional effects.

The present invention relates to the design and synthesis of 1,3-substituted oligomers derived from 1,2,3-triazoles, as shown in FIGS. 1A-C. Solution NMR studies (see Example 9) on trimers and tetramers suggest that these oligomers adopt zigzag conformations reminiscent of peptide β-strands. Dipole-dipole interactions between neighboring triazole rings appear to play a critical role in stabilizing the observed conformations in polar solvents such as DMSO and acetone.

In at least one aspect of the present invention, converting the compound of Formula II with an azide-producing compound and the compound of Formula III involves converting the compound of Formula II with the azide-producing compound to produce a compound of Formula IV:

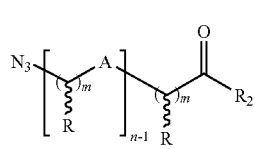

and then reacting the compound of Formula IV with the compound of Formula III to produce the compound of Formula I.

Suitable azide-producing compounds include, for example, triflic acid and azide ions.

The compound of Formula II may be converted to the compound of Formula IV using methods that will be apparent to one of ordinary skill in the art. For example, the compound of Formula II may be converted to the compound of Formula IV with triflic azide. This may be done, for example, in the presence of copper (II), nickel (II), or zinc (II) ions (see Alper et al., *Tetrahedron Lett.*, 37:6029-6032 (1996); Zaloom & Roberts, *J. Org. Chem.* 46:5173-5176 (1981); Nyffeler et al., *J. Am. Chem. Soc.* 124:10773-10778 (2002), which are hereby incorporated by reference in their entirety). As another example, the compound of Formula II may be converted to the compound of Formula IV by converting the compound of Formula II to a corresponding 2-((p-nitrobenzene)sulfonyl) oxyester and reacting the corresponding 2-((p-nitrobenzene)sulfonyl)oxyester with an azide ion to produce the compound of Formula IV (see Hoffman & Kim, *Tetrahedron* 48:3007-3020 (1992), which is hereby incorporated by reference in its entirety).

In at least one preferred embodiment of this aspect of the present invention, the protecting group of Formula II is removed to produce an amine compound of Formula V:

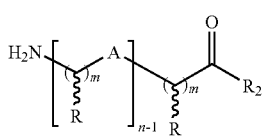

V before converting to the azide of Formula IV. The amine can be converted to the corresponding azide of Formula IV by reacting the amine with the azide-producing compound as described above (see Alper et al., *Tetrahedron Lett.,* 37:6029-6032 (1996); Zaloom & Roberts, *J. Org. Chem.* 46:5173-5176 (1981); Nyffeler et al., *J. Am. Chem. Soc.* 124:10773-10778 (2002); Hoffman & Kim, *Tetrahedron* 48:3007-3020 (1992), which are hereby incorporated by reference in their entirety).

The compound of Formula IV may be reacted with the compound of Formula III to produce the compound of Formula I using standard metal catalyzed Huisgen azide-alkyne [2+3] cycloaddition (e.g., Rostovtsev et al., *Angew. Chem., Int. Ed.* 41:2596 (2002) (reacting in the presence of copper (I)); Zhang et al., *J. Am. Chem. Soc.* ASAP Article (2005) (reacting in the presence of ruthenium (II)), which are hereby incorporated by reference in their entirety).

In aspects of the present invention in which "n" in the compound of Formula I is 2, the compound of Formula II may be prepared by providing a compound of Formula VI:

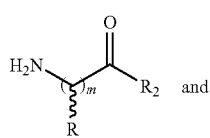

VI converting the compound of Formula VI with an azide-producing compound and the compound of Formula III to produce the compound of Formula II. The compound of Formula VI can be converted with the azide-producing compound and the compound of Formula III using the methods described above.

Suitable protecting groups according to this and all aspects of the present invention include, e.g., tert-butyloxycarbonyl ("Boc"), 9-fluorenylmethyloxycarbonyl ("Fmoc"), carbobenzyloxy ("Cbz"), and trityl.

Amino acid side chains according to this and all aspects of the present invention can be any amino acid side chain-from natural or nonnatural amino acids-including alpha amino acids, beta amino acids, gamma amino acids, L-amino acids, and D-amino acids.

Another aspect of the present invention relates to an oligomer having the Formula I. In at least one preferred embodiment of this aspect of the present invention, n is any number from 2 through 8.

The oligomers according to this aspect of the present invention may be made by the methods described above.

The present invention contemplates non-peptidic oligomers that include, e.g., linear and/or helical (e.g., mimics of: β-strands, α-helix, $3_{10}$ helices) conformations.

Accumulating structural evidence on the conformational properties of triazolamers suggests that trimers and tetramers adopt stable extended conformations but that turn conformations start to appear in longer oligomers (see Example 11). The stability of tetramers in extended conformations provides an opportunity to test the biological potential of these compounds as protein inhibitors. Many proteins are recognized when in β-strand conformations. Thus, it is contemplated that the methods of the present invention may be used to prepare non-peptidic oligomers that mimic the β-strand conformation of proteins, which could be used to inhibit the activity of the proteins. As will be apparent to one of ordinary skill in the art, suitable non-peptidic oligomer protein inhibitors may be designed to mimic the known or predicted conformation of a protein's β-strand, which oligomer would compete with the protein for interaction with other molecules, thereby inhibiting the protein's activity.

Suitable protein inhibitors of this aspect of the present invention include, for example, protease inhibitors. Proteases typically recognize and cleave peptides in β-strand conformations and, in general, four to five residues provide the majority of the binding interactions (Tyndall et al., "Proteases Universally Recognize Beta Strands in Their Active Sites," *Chem. Rev.* 105:973-99 (2005), which is hereby incorporated by reference in its entirety). It is contemplated that the methods of the present invention may be used to prepare non-peptidic oligomers that mimic the β-strand conformation of proteins targeted by proteases, which oligomers could be used to inihibit the activity of the proteases. As will be apparent to one of ordinary skill in the art, given the sequence of the protease, the sequence of the protein targeted by the protease, and/or the sequence of an inhibitor of the protease, suitable non-peptidic oligomer protease inhibitors may be designed. For example, non-peptidic oligomer proteases may be designed to: (i) mimic the known or predicted conformation of a protein targeted by a protease (preferably a natural substrate sequence), (ii) mimic the known or predicted conformation of an active site (i.e., a site that confers protease inhibitor activity) of a protease inhibitor, and/or (iii) interact with (e.g., bind to) the known or predicted conformation of a binding site (i.e., a site that binds to a protein that is cleaved by the protease) of a protease.

Preferred non-peptidic protein inhibitors of the present invention include triazolamers 8-10, those that mimic a β-strand of the proteins set forth in Table 1 (e.g., the exemplary non-peptidic oligomer protein inhibitors set forth in Table 1), those that interact with an active site (e.g., that mimic a natural substrate sequence) of the proteases set forth in Table 2 (e.g., the exemplary non-peptidic oligomer protease inhibitors set forth in Table 2), and those that mimic the protease inhibitors set forth in Table 3 (e.g., the exemplary non-peptidic oligomer protease inhibitors set forth in Table 3).

TABLE 1

Exemplary β-Strands and Non-peptidic β-Strand Mimics

| Protein | Protein Data Bank ID | β-Strand Residues | Exemplary Non-peptidic Oligomer Protein Inhibitor |
|---------|---------------------|-------------------|---------------------------------------------------|
| E7 | 1GUX | 22-28 | |
| HIV-1 Tat | 1TBC | 47-57 | |
| Peptide YEEI | 1SPS | 4-7 | |

TABLE 2
Exemplary Proteases and Potential Non-peptidic Inhibitors
| Protease | Protein Data Bank ID | Natural Substrate Sequence | Exemplary Non-peptidic Oligomer Protease Inhibitor |
|---|---|---|---|
| HIV-1 Protease | 1HHP | (Ser or Thr)-Xaa-Xaa-(Tyr or Phe)-(Xaa Xaa is any amino acid) | 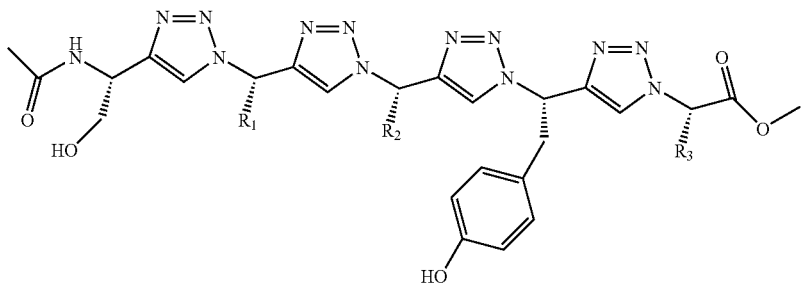 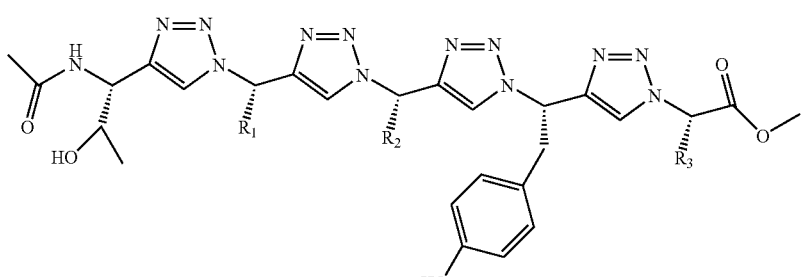 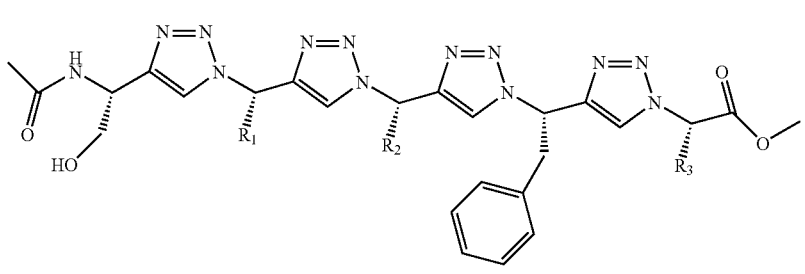 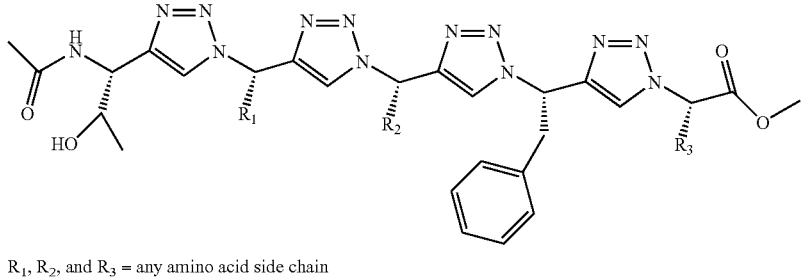 $R_1$, $R_2$, and $R_3$ = any amino acid side chain |
| Chymotrypsin | 1GMD | (Phe or Tyr or Trp)-(Xaa Xaa is any amino acid) | 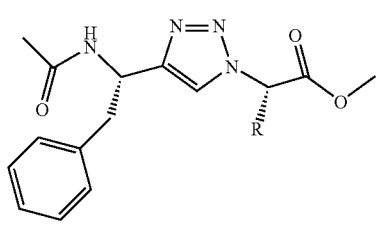 |

TABLE 2-continued
Exemplary Proteases and Potential Non-peptidic Inhibitors
| Protease | Protein Data Bank ID | Natural Substrate Sequence | Exemplary Non-peptidic Oligomer Protease Inhibitor |
|---|---|---|---|
| | | | 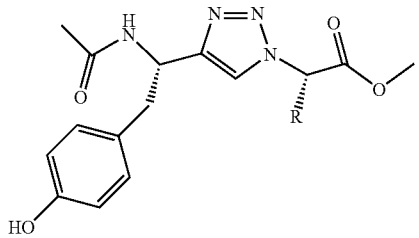 |
| 20S Proteasome | 1IRU | Leu-Leu-Val-Tyr (SEQ ID NO: 1) | 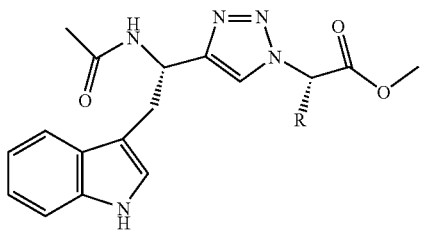 |
| Renin | 1BBS | His-Xaa-Phe-His-Leu-Leu-Val-Tyr (SEQ ID NO: 2) Xaa is any amino acid | 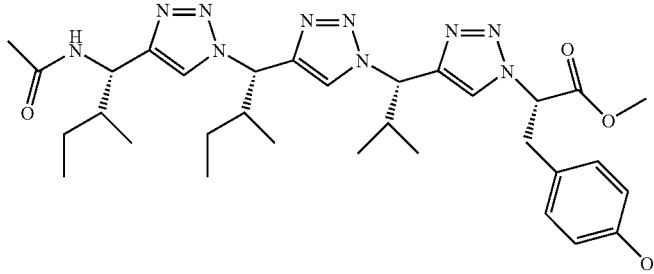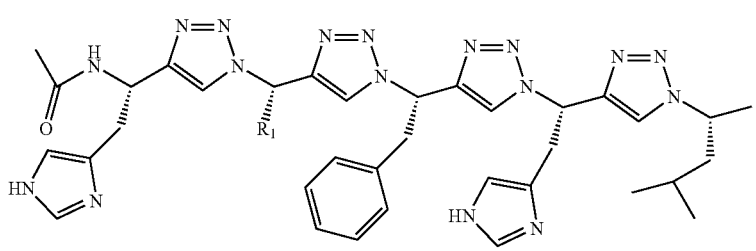 |
$R_1$ = any amino acid side chain

TABLE 3

Exemplary Protease Inhibitors

| Protease Inhibitor | Protein Data Bank ID | Active Site | Non-peptidic Oligomer Protease Inhibitor |
|---|---|---|---|
| A-74704 | 9HVP | Val-Phe-Phe-Val (SEQ ID NO: 3) | |
| Ac-Leu-Phe-CF$_3$ | 7GCH | Leu-Phe | |
| Calpain-Inhibitor I | 1J2Q | Ile-Ile-Nle | |
| CGP 38'560 | 1RNE | Phe-His-Cha-Val | |

With reference to Table 1, the human papillomavirus E7 oncoprotein ("E7") binds the retinoblastoma tumor suppressor thereby inactivating it; this event is associated with over 90% of cervical cancer cases. Binding is mediated by a conserved LxCxE sequence in an extended conformation. Non-peptidic oligomer protein inhibitors of the present invention that mimic E7 (preferably residues 22-28), for example the oligomer set forth in Table 1, may therefore inhibit cell transformation via this mechanism.

The HIV-1 Tat protein binds to the transcriptional activator-responsive element allowing for the transcription of proviral DNA. This essential step in the HIV-1 life cycle may be interrupted by mimics of HIV-1 Tat. Non-peptidic oligomers of the present invention that mimic the HIV-1 Tat protein (preferably residues 47-57), for example the oligomer set forth in Table 1, may be useful to interrupt the life cycle of HIV-1.

SH2 domains recognize phosphorylated tyrosine ("pY") residues and are important for protein tyrosine kinase signal propagation. Peptides containing the pYEEI sequence ("Peptide YEEI") bind to SH2. Non-peptidic oligomers of the present invention that mimic Peptide YEEI (preferably residues 4-7), for example the oligomer set forth in Table 1, that disrupt SH2-mediated signaling pathways would be valuable tools for the study of such pathways.

With reference to Tables 2 and 3, HIV-1 Protease is essential for virus maturation. Inhibition of this enzyme results in the production of non-infectious virus particles. A-74704 is a powerful inhibitor of HIV-1 Protease and provides a template for the development of new inhibitor compounds. Non-peptidic oligomer protease inhibitors of the present invention that interact with HIV-1 Protease (e.g., the oligomers set forth in Table 2) and/or that mimic A-74704 (e.g., the oligomer set forth in Table 3), may be useful to inhibit HIV-1 Protease.

Chymotrypsin is a digestive enzyme that has been extensively studied and is readily available. Inhibitors similar to Ac-Leu-Phe-CF$_3$ will be developed with the intent to gather crystallographic data in order to demonstrate the mode of binding of this class of inhibitors. Non-peptidic oligomer protease inhibitors of the present invention that interact with chymotrypsin (e.g., the oligomers set forth in Table 2) and/or that mimic Ac-Leu-Phe-CF$_3$ (e.g., the oligomer set forth in Table 3), may be useful to inhibit chymotrypsin.

Inhibition of the 20S Proteasome (by compounds such as Calpsin-Inhibitor I) has been hypothesized to be useful for a variety of a range of diseases such as cancer and neurodegenerative disorders. Non-peptidic oligomer protease inhibitors of the present invention that interact with 20S Proteasome (e.g., the oligomer set forth in Table 2) and/or that mimic Calpsin-Inhibitor I (e.g., the oligomer set forth in Table 3), may be useful to inhibit 20S Proteasome and to treat these diseases.

Renin is necessary for the production of angiotensin II, a hormone that causes vasoconstriction and can lead to high blood pressure. Renin inhibitors such as CGP 38'560 are therefore potential therapeutic agents for the treatment of hypertension. Non-peptidic oligomer protease inhibitors of the present invention that interact with Renin (e.g., the oligomer set forth in Table 2) and/or that mimic CGP 38'560 (e.g., the oligomer set forth in Table 3), may be useful to inhibit renin and to treat these diseases.

Another aspect of the present invention relates to a method of inhibiting a protein (e.g., a protease) by contacting the protein (e.g., the protease) with a non-peptidic oligomer protein inhibitor of the present invention under conditions effective to inhibit the protein.

The present invention may be further illustrated by reference to the following examples.

EXAMPLES

Example 1

Materials and Methods

Commercial-grade reagents and solvents were used without further purification except as indicated. Dichloromethane ("DCM"), tetrahydrofuran ("THF"), and DMF were dried prior to use by percolation through anhydrous Al$_2$O$_3$ as described by Grubbs and coworkers (Pangbom et al., *Organometallics* 15:1518-1520 (1996), which is hereby incorporated by reference in its entirety). All reactions were stirred magnetically; moisture-sensitive reactions were performed under nitrogen in flame-dried glassware. Unless indicated, all reactions were performed at room temperature. Thin-layer chromatography ("TLC"), using ethyl acetate:hexane, ethyl acetate:DCM or methanol:DCM as the solvent system, was used to monitor reactions. Visualization was accomplished by either ultraviolet light or by immersing the plate in a 1% aqueous solution of potassium permanganate and heating. Flash chromatography with silica gel was performed following the conditions described by Still and coworkers (Still et al., *J. Org. Chem.* 43:2923-2925 (1978), which is hereby incorporated by reference in its entirety). Solvents were removed by rotary evaporation under reduced pressure; where appropriate, the residue was further dried using a vacuum pump.

$^1$H NMR DFQ-COSY, $^1$H NMR TOCSY, and $^1$H NMR ROESY studies were performed on a Bruker Avance 400 (400 MHz) spectrometer. Carbon NMR spectra were obtained on a Bruker (100 MHz) spectrometer. Infrared ("IR") spectra were obtained with a Thermo Nicolet Avatar 360 FTIR. High-resolution mass spectra ("HRMS") were obtained on a LC/MSD TOF (Agilent Technologies). Low-resolution mass spectra ("LRMS") data was obtained on an Agilent 1100 series LC/MSD (XCT) electrospray trap.

DFQ-COSY spectra were recorded at 298 K with the delay for evolution of long-range correlations set to 200 milliseconds and were acquired with 2,000 points in the f1 domain and 256 points in the f1 domain. The data were processed using Bruker XWINNMR software on an HP Workstation X1100. A 90° sine-squared window function was applied in both directions. The data were zero-filled once in the f1 domain to give a final matrix of 1,000 by 1,000 real points.

TOCSY spectra were recorded at 298 K with a mixing time of 80 milliseconds and were acquired with 2,000 points in the f2 domain and 256 points in the f1 domain. The data were processed using Bruker XWINNMR software on a HP Workstation X1100. A 90° sine-squared window function was applied in both directions. The data were zero-filled to give a final matrix of 1,000 by 1,000 real points.

ROESY spectra were recorded at 298 K with a mixing time of 200 milliseconds and were acquired with 2,000 points in the f2 domain and 256 points in the f1 domain. The data were processed using Bruker XWINNMR software on an HP Workstation X1100. A 90° sine-squared window function was applied in both directions. The data were zero-filled once in the f1 domain to give a final matrix of 1,000 by 1,000 real points.

Proton chemical shifts are reported as d values relative to tetramethylsilane (0.00 ppm) or to the particular solvent used in the experiment. Carbon chemical shifts are reported as d values relative to the particular solvent used in the experiment (CDCl$_3$: 77.0 ppm). Data is reported as follows: chemical shift, multiplicity (s=singlet, d=doublet, t=triplet, q=quartet, m=multiplet, dd=doublet of doublet, br=broad), coupling constant, and integration.

Example 2

Synthesis of 1,3 Substituted Oligomers 1,3-substituted oligomers were prepared from amino acid methyl esters through an iterative reaction sequence, shown in Scheme 1, consisting of conversion of the amine to the corresponding azide (Alper et al., *Tetrahedron Lett.* 37:6029-6032 (1996), which is hereby incorporated by reference in its entirety), copper(1)-catalyzed azide-alkyne [3+2] cycloaddition (Wang et al., *J. Am. Chem. Soc.* 125:3192-3193 (2003), which is hereby incorporated by reference in its entirety) with the suitable amino alkyne 1a or 1b, followed by removal of the protecting group. To examine the solution conformations of short 1,3-substituted triazole oligomers, two trimers (3a and 3b) and two tetramers (4a and 4b) were prepared and studied as described in Examples 3-9.

Scheme 1

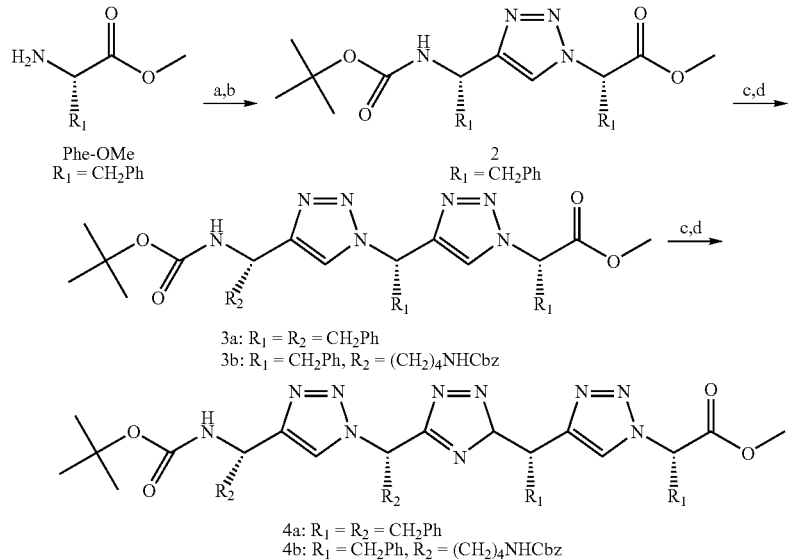

a: TfN$_3$, DCM, CuSO$_4$, TEA
b: Alkyne 1a, CuSO$_4$·5H$_2$O, sodium L-ascorbate, TBTA
c: i. 30%-50% TFA in DCM; ii. TfN$_3$, DCM, CuSO$_4$, TEA
d: Alkyne 1a or 1b, CuSO$_4$·5H$_2$O, sodium L-ascorbate, TBTA

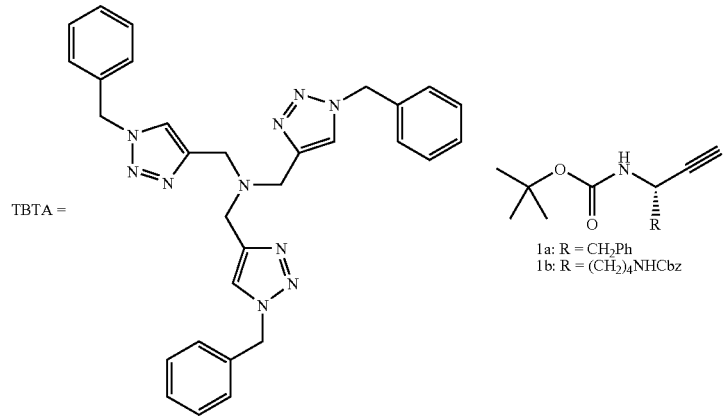

Example 3

Synthesis of Alkynes 1a and 1b

The amino alkynes 1a ($^1$H NMR (400 MHz, CDCl$_3$) δ 7.25-7.15 (m, 5H), 4.68 (br s, 1H), 4.60 (br s, 1H), 2.91 (dd, AB pattern, J=13.2, 5.4 Hz, 1H), 2.86 (dd, AB pattern, J=13.3, 7.1 Hz, 1H), 2.19 (d, J=2.2, 1H), 1.35 (s, 9H); $^{13}$C NMR (100 MHz, CDCl$_3$) δ 154.62, 136.37, 129.81, 128.59, 126.91, 82.82, 80.01, 72.21, 43.88, 41.73, 28.35; LRMS m/z for C$_{15}$H$_{19}$NO$_2$ [M+Na]$^+$, calcd 268.1, found 268.1) and 1b ($^1$H NMR (400 MHz, CDCl$_3$) δ 7.23-7.17 (m, 5H), 5.22 (br t, 1H), 5.03 (br t, 1H), 5.01 (s, 2H), 4.28 (br q, 1H), 3.05 (br q, 2H), 2.19 (d, J=2.3 Hz, 1H), 1.56-1.49 (m, 2H), 1.41-1.35 (m, 2H), 1.34 (s, 9H), 1.33-1.17 (m, 2H); $^{13}$C NMR (100 MHz, CDCl$_3$) δ 156.57, 154.98, 136.73, 128.44, 127.02, 127.98, 83.54, 79.74, 71.18, 66.43, 40.74, 35.55, 30.33, 29.31, 28.42, 22.66; LRMS m/z for C$_{20}$H$_{28}$N$_2$O$_4$ [M+Na]$^+$, calcd 383.2, found 383.2) were prepared as shown in Scheme 2 from the aminoaldehydes by the Corey-Fuchs homologation reaction as described in Reginato et al., *Tetrahedron Lett.* 52:10985-10996 (1996) (1a), which is hereby incorporated by reference in its entirety and Hauske et al., *Tetrahedron Lett.* 33: 3715-3716 (1992) (1b), which is hereby incorporated by reference in its entirety.

Scheme 2

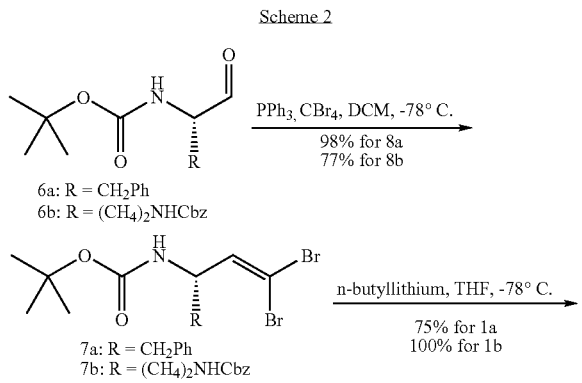

-continued

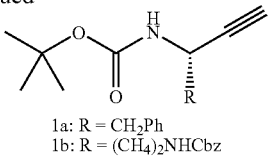

1a: R = CH₂Ph
1b: R = (CH₄)₂NHCbz

Example 4

Synthesis of Boc Dimer Methyl Ester 2

H-Phe-OMe.HCl (125 mg, 0.580 mmol) was dissolved in a solution of triflic azide (Alperet al., *Tetrahedron Lett.* 37:6029-6032 (1996), which is hereby incorporated by reference in its entirety) (9.30 mmol) in DCM (25 mL). Triethylamine ("TEA") (0.33 mL, 2.32 mmol) and CuSO$_4$.5H$_2$O (28 mg, 0.12 mmol) were added and the reaction mixture was stirred for 16 hours. The reaction mixture was concentrated under vacuum and the residue was purified by column chromatography (DCM, 100%) to yield azido methyl ester as a colorless oil (50 mg, 42%) ($^1$H NMR (400 MHz, CDCl$_3$) δ 7.35-7.22 (m, 5H), 4.06 (dd, J=8.7, 5.4 Hz, 1H), 3.77 (s, 3H), 3.17 (dd, AB pattern, J=14.0, 5.4 Hz, 1H), 3.01 (dd, AB pattern, J=14.0, 8.8 Hz, 1H); IR (film) 2104, 1741 cm$^{-1}$).

To a solution of azido methyl ester (50 mg, 0.25 mmol) and alkyne 1a (181 mg, 0.740 mmol) in tert-butanol (2 mL) was added a solution of CuSO$_4$.5H$_2$O (184 mg, 0.740 mmol) and tris-(1-benzyl-1H-[1,2,3]triazol-4-ylmethyl)-amine ("TBTA") (Chan et al., *Org. Lett.* 6:2853-2855 (2004), which is hereby incorporated by reference in its entirety) (391 mg, 0.740 mmol) in 2:1 tert-butanol:water (30 mL). Sodium L-ascorbate (292 mg, 1.47 mmol) was added and the reaction mixture was stirred for 16 hours. Brine (30 mL) was added and the mixture was extracted with DCM (3×30 mL). The combined organic layers were dried over MgSO$_4$, filtered, and concentrated under vacuum to afford a yellow oil. The oil was purified by column chromatography (ethyl acetate:DCM, 5:95) to yield Boc dimer methyl ester 2 as a white solid (84 mg, 76%) ($^1$H NMR (400 MHz, CDCl$_3$) δ 7.40-7.13 (m, 7H), 7.03-6.97 (m, 4H), 5.45 (t, J=7.4 Hz, 1H), 5.29 (s br, 1H), 5.03 (q, J=7.1 Hz, 1H), 3.71 (s, 3H), 3.46 (dd, J=14.1, 6.2 Hz, 1H), 3.40 (dd, AB pattern, J=14.1, 8.9 Hz, 1H), 3.28-3.25 (m br, 1H), 3.10-3.06 (m br, 1H), 1.41 (s, 9H);$^{13}$C NMR (100 MHz, CDCl$_3$) δ 185.05, 168.45, 155.12, 147.48, 137.26, 134.80 129.58, 128.87, 128.78, 128.26, 127.52, 126.48, 121.39, 79.60, 64.03, 53.03, 48.69, 41.73, 38.59, 28.34; HRMS m/z for C$_{25}$H$_{31}$N$_4$O$_4$ [M+H]$^+$, calcd 451.2339, found 451.2333).

Example 5

Synthesis of Boc Trimer Methyl Ester 3a

Boc dimer methyl ester 2 (84 mg, 0.19 mmol) was dissolved in a 30% trifluoroacetic acid ("TFA") solution in DCM. The reaction mixture was stirred for 1 hour, dried under vacuum, then redissolved in a 5% N,N-diisopropyl ethylamine ("DIPEA") solution in DCM. The reaction mixture was dried under vacuum and the residue was dissolved in a solution of triflic azide (2.98 mmol) in DCM (8 mL). TEA (0.10 mL, 0.75 mmol) and CuSO$_4$.5H$_2$O (9 mg, 0.04 mmol) were added and the reaction mixture was stirred for 16 hours. The reaction mixture was concentrated under vacuum and the residue was purified by column chromatography (DCM, 100%) to yield azido dimer methyl ester as a colorless oil (56 mg, 79%) ($^1$H NMR (400 MHz, CDCl$_3$) δ 7.47 (s, 1H), 7.28-7.22 (m, 6H), 7.19-7.16 (m, 2H), 6.98-6.96 (m, 2H), 5.57 (dd, J=8.7, 6.1 Hz, 1H), 4.86 (dd, J=8.4, 5.7 Hz, 1H), 3.76 (s, 3H), 3.51-3.43 (m, 2H), 3.27 (dd, AB pattern, J=13.9, 5.8 Hz, 1H), 3.13 (dd, J=17.2, 8.4 Hz, 0.5H), 3.07 (dd, J=17.1, 8.4 Hz, 0.5H); IR (film) 2090, 1730 cm$^{-1}$).

To a solution of azido dimer methyl ester (56 mg, 0.15 mmol) and alkyne 1a (109 mg, 0.444 mmol) in DMF (2 mL) was added a solution of TBTA (176 mg, 0.888 mmol) in DMF (8 mL). A solution of CuSO$_4$.5H$_2$O (111 mg, 0.444 mmol) in water (1 mL) and a solution of sodium L-ascorbate (176 mg, 0.888 mmol) in water (1 mL) were then added and the reaction mixture was stirred for 16 hours. Brine (10 mL) was added and the mixture was extracted with DCM (3×10 mL). The combined organic layers were dried over MgSO$_4$, filtered, and concentrated under vacuum to afford a yellow oil. The oil was purified by column chromatography (ethyl acetate:hexanes, 1:1) to yield Boc trimer methyl ester 3a as a white solid (41 mg, 45%) ($^1$H NMR (400 MHz, DMSO-$_{d6}$) δ 8.34 (s, 1H), 7.90 (s, 1H), 7.26-7.20 (m, 3H), 7.19-7.13 (m, 8H), 7.12-7.07 (m, 2H), 7.06-7.00 (m, 2H), 6.18 (t, J=7.8 Hz, 1H), 5.82 (dd, J=10.6, 5.2 Hz, 1H), 4.82 (q, J=8.8 Hz, 1H), 3.69 (s, 3H), 3.57-3.50 (m, 3H), 3.43 (dd, J=14.1, 10.7 Hz, 1H), 3.07 (dd, AB pattern, J=13.6, 5.6 Hz, 1H), 2.94 (dd, AB pattern, J=13.7, 9.4 Hz, 1H), 1.29 (s, 9H); $^{13}$C NMR (100 MHz, DMSO-$_{d6}$) δ 168.43, 154.80, 148.79, 144.86, 138.26, 136.39, 135.50, 129.11, 128.95, 128.72, 128.20, 128.09, 127.87, 126.75, 126.52, 125.93, 123.80, 120.84, 77.67, 63.10, 57.38, 52.80, 48.44, 40.50, 36.65, 28.07; HRMS m/z for C$_{35}$H$_{40}$N$_7$O$_4$ [M+H]$^+$, calcd 622.3136, found 622.3132).

Example 6

Synthesis of Boc Tetramer Methyl Ester 4a

Boc trimer methyl ester 3a (41 mg, 0.066 mmol) was dissolved in a 50% TFA solution in DCM. The reaction mixture was stirred for 1 hour, dried under vacuum, then redissolved in a 5% DIPEA solution in DCM. The reaction mixture was dried under vacuum and the residue was dissolved in a solution of triflic azide (1.06 mmol) in DCM (3 mL). TEA (0.037 mL, 0.27 mmol) and CuSO$_4$.5H$_2$O (3 mg, 0.01 mmol) were added and the reaction mixture was stirred for 16 hours. The reaction mixture was dried under vacuum and the residue was purified by column chromatography (ethyl acetate: DCM, 10:90) to yield azido trimer methyl ester as a colorless oil (28 mg, 76%) ($^1$H NMR (400 MHz, CDCl$_3$) δ 7.56 (s, 0.5H), 7.54 (s, 0.5H), 7.44 (s, 0.5H), 7.43 (s, 0.5H), 7.41-7.13 (m, 11H), 6.99-6.88 (m, 4H), 6.09 (br s, 1H), 5.99-5.94 (m, 1H), 5.55 (dd, J=8.5, 7.2 Hz, 1H), 4.86-4.81 (m, 1H), 3.75 (s, 3H), 3.61-3.52 (m, 2H), 3.50-3.46 (m, 1H), 3.44-3.36 (m, 1H), 3.25 (dd, AB pattern J=13.9, 5.7 Hz, 1H), 3.10 (dd, AB pattern, J=13.8, 8.6 Hz, 1H) ; IR (film) 2100, 1750 cm$^{-1}$).

To a solution of azido trimer methyl ester (28 mg, 0.050 mmol) and alkyne 1a (74 mg, 0.30 mmol) in DMF (2 mL) was added a solution of TBTA (160 mg, 0.30 mmol) in DMF (8 mL). A solution of CuSO$_4$.5H$_2$O (76 mg, 0.30 mmol) in water (1 mL) and a solution of sodium L-ascorbate (120 mg, 0.60 mmol) in water (1 mL) were added and the reaction mixture was stirred for 16 hours. Brine (5 mL) was added and the mixture was extracted with DCM (3×5 mL). The combined organic layers were dried over MgSO$_4$, filtered, and dried under vacuum to afford a yellow oil. The oil was purified by column chromatography (ethyl acetate:hexanes, 1:1) to yield Boc tetramer methyl ester 4a as a white solid (30 mg, 75%)

(¹H NMR (400 MHz, Acetone-$d_6$) δ 7.97 (s, 1H), 7.84 (s, 0.3H), 7.82 (s, 0.7H), 7.60 (br s, 1H), 7.10-7.06 (m, 16H), 7.04-6.96 (m, 1H), 6.95-6.92 (m, 3H), 6.12-6.09 (br d, J=8.4 Hz, 1H), 6.03 (t, J=7.7 Hz, 1H), 5.98 (t, J=8.0 Hz, 1H), 5.62-5.58 (dd, J=10.1, 5.4 Hz, 1H), 4.89 (q, J=7.8 Hz, 1H), 3.60 (s, 3H), 3.49-3.47 (m, 5H), 3.37 (dd, J=10.2, 7.1 Hz, 1H), 3.05 (dd, AB pattern, J=13.5, 6.3 Hz, 1H), 2.96 (dd, AB pattern, J=13.4, 8.0 Hz, 1H), 1.20 (s, 9H); ¹³C NMR (100 MHz, CDCl$_3$) δ 168.24, 155.05, 144.95, 144.59, 144.37, 137.33, 136.03, 135.67, 135.62, 134.36, 134.29, 129.55, 129.04, 129.02, 128.93, 128.87, 128.83, 128.64, 128.59, 128.24, 127.70, 127.26, 127.13, 126.46, 123.13, 122.85, 122.28, 120.94, 79.54, 64.18, 64.14, 59.39, 59.08, 53.18, 53.15, 48.71, 42.23, 41,96, 41.62, 39.04, 38.81, 28.35; HRMS m/z for $C_{45}H_{48}N_{10}O_4$ [M+H]$^+$, calcd 793.3932, found 793.3953).

Example 7

Synthesis of Boc Trimer Methyl Ester 3b

Boc dimer methyl ester 2 (89 mg, 0.20 mmol) was dissolved in a 30% TFA solution in DCM. The reaction mixture was stirred for 1 hour, dried under vacuum, then redissolved in a 5% DIPEA solution in DCM. The reaction mixture was dried under vacuum and the residue was dissolved in a solution of triflic azide (2.98 mmol) in DCM (8 mL). TEA (0.10 mL, 0.75 mmol) and CuSO$_4$.5H$_2$O (9 mg, 0.04 mmol) were added and the reaction mixture was stirred for 16 hours. The reaction mixture was concentrated under vacuum and the residue was purified by column chromatography (DCM, 100%) to yield azido dimer methyl ester as a colorless oil (56 mg, 79%) (¹H NMR (400 MHz, CDCl$_3$) δ 7.47 (s, 1H), 7.28-7.22 (m, 6H), 7.19-7.16 (m, 2H), 6.98-6.96 (m, 2H), 5.57 (dd, J=8.7, 6.1 Hz, 1H), 4.86 (dd, J=8.4, 5.7 Hz, 1H), 3.76 (s, 3H), 3.51-3.43 (m, 2H), 3.27 (dd, AB pattern, J=13.9, 5.8 Hz, 1H), 3.13 (dd, J=17.2, 8.4 Hz, 0.5H), 3.07 (dd, J=17.1, 8.4 Hz, 0.5H); IR (film) 2090, 1730 cm$^{-1}$).

To a solution of azido dimer methyl ester (54 mg, 0.14 mmol) and alkyne 1b (104 mg, 0.29 mmol) in tert-butanol (20 mL) was added TBTA (154 mg, 0.29 mmol). A solution of CuSO$_4$.5H$_2$O (36 mg, 0.15 mmol) in water (5 mL) and a solution of sodium L-ascorbate (57 mg, 0.29 mmol) in water (5 mL) were then added and the reaction mixture was stirred for 48 hours. Brine (20 mL) was added and the mixture was extracted with DCM (3×20 mL). The combined organic layers were dried over MgSO$_4$, filtered, and concentrated under vacuum to afford a yellow oil. The oil was purified by column chromatography (methanol:ethyl acetate, 1:20) to yield Boc trimer methyl ester 3b as a white solid (100.3 mg, 94%) (¹H NMR (400 MHz, Acetone-$d_6$) δ 8.08 (s, 1H), 7.77 (s, 1H), 7.36-7.28 (m, 4H), 7.22-7.17 (m, 7H), 7.16-7.05 (m, 4H), 6.31 (br s, 1H), 6.19-6.17 (d, J=8.4 Hz, 1H), 6.13 (t, J=7.9 Hz, 1H), 5.72 (dd, J=10.1, 5.5 Hz, 1H), 5.05 (s, 2H), 4.76 (q, J=7.0 Hz, 1H), 3.72 (s, 3H), 3.63-3.58 (m, 3H), 3.51 (dd, AB pattern, J=14.2, 10.1 Hz, 1H), 3.13 (q, J=6.9 Hz, 2H), 1.89-1.78 (m, 2H), 1.56-1.49 (m, 2H), 1.39 (s, 9H), 1.35-1.29 (m, 2H); ¹³C NMR (100 MHz, CDCl$_3$) δ 168.29, 156.43, 155.33, 145.04, 136.66, 135.96, 134.44, 129.08, 129.01, 128.88, 128.84, 128.83, 128.60, 128.51, 128.35, 128.12, 128.07, 127.67, 127.16, 122.87, 120.93, 79.59, 66.59, 64.17, 59.20, 53.16, 46.82, 42.10, 40.77, 38.76, 35.69, 35.16, 29.41, 28.38, 22.79; HRMS m/z for $C_{40}H_{49}N_8O_6$ [M+H]$^+$, calcd 737.3769, found 737.3760).

Example 8

Synthesis of Boc Tetramer Methyl Ester 4b

Boc trimer methyl ester 3b (49 mg, 0.070 mmol) was dissolved in a 50% TFA solution in DCM. The reaction mixture was stirred for 1 hour, concentrated under vacuum, then redissolved in a 5% DIPEA solution in DCM. The reaction mixture was concentrated under vacuum and the residue was dissolved in a solution of triflic azide (1.06 mmol) in DCM (2.2 mL). TEA (0.037 mL, 0.27 mmol) and CuSO$_4$ (2 mg, 0.01 mmol) were added and the reaction mixture was stirred for 16 hours. The reaction mixture was dried under vacuum and the residue was purified by column chromatography (ethyl acetate:DCM, 10:90) to yield azido trimer methyl ester as a colorless oil (47.5 mg, 100%) (¹H NMR (400 MHz, CDCl$_3$) δ 7.56 (br s, 1H), 7.43 (br s, 1H), 7.30-7.23 (m, 4H), 7.15-7.10 (m, 7H), 6.92-6.84 (m, 4H), 5.90 (t, J=3.0 Hz, 1H), 5.48 (dd, J=8.8, 6.2 Hz, 1H), 5.01 (s, 2H), 4.78 (t, J=5.6 Hz, 1H), 4.48 (t, J=6.9 Hz, 1H), 3.68 (s, 3H), 3.54 (d, J=7.5 Hz, 2H), 3.43 (dd, AB pattern, J=14.2, 6.2 Hz, 1H), 3.37 (dd, AB pattern, J=14.2, 8.8 Hz, 1H), 3.12-3.06 (m, 2H), 1.78 (q, J=7.5 Hz, 2H), 1.47-1.42 (m, 2H), 1.34-1.18 (m, 2H); IR (film) 2101, 1737 cm$^{-1}$).

To a solution of azido trimer methyl ester (47.5 mg, 0.070 mmol) and alkyne 1b (52 mg, 0.14 mmol) in tert-butanol (18 mL) was added TBTA (74 mg, 0.14 mmol). A solution of CuSO$_4$.5H$_2$O (18 mg, 0.070 mmol) in water (2 mL) and a solution of sodium L-ascorbate (28 mg, 0.14 mmol) in water (2 mL) were added and the reaction mixture was stirred for 16 hours. Brine (20 mL) was added and the mixture was extracted with DCM (3×20 mL). The combined organic layers were dried over MgSO$_4$, filtered, and concentrated under vacuum to afford a yellow oil. The oil was purified by column chromatography (methanol:ethyl acetate, 1:20) to yield Boc tetramer methyl ester 4b as a white solid (36.9 mg, 50%) (¹H NMR (400 MHz, DMSO-$d_6$) δ 8.37 (s, 1H), 8.17 (s, 1H), 7.83 (s, 1H), 7.38-7.30 (m, 9H), 7.22-7.19 (m, 2H), 7.15-7.11 (m, 5H), 7.07-7.01 (m, 4H), 6.19 (t, J=8.1 Hz, 1H), 5.84 (t, J=5.3 Hz, 1H), 5.82-5.81 (m, 1H), 5.00 (s, 4H), 4.68-4.54 (br q, 1H), 3.69 (s, 3H), 3.56-3.52 (m, 3H), 3.45 (dd, AB pattern, J=14.3, 10.4 Hz, 1H), 2.97-2.92 (m, 4H), 2.17 (q, J=7.6 Hz, 2H), 1.83-1.71 (m, 1H), 1.70-1.58 (m, 1H), 1.50-1.17 (m, 6H), 1.37 (s, 9H), 1.16-1.05 (m, 1H), 1.04-0.96 (m, 1H); ¹³C NMR (100 MHz, DMSO-$d_6$) δ 168.51, 156.02, 155.18, 149.53, 145.17, 144.66, 137.25, 137.21, 136.30, 135.54, 128.98, 128.78, 128.31, 128.26, 128.14, 127.69, 126.83, 126.62, 124.00, 122.56, 120.35, 77.74, 65.08, 65.05, 63.15, 57.78, 56.17, 52.88, 46.90, 36.67, 34.56, 34.20, 29.06, 28.66, 28.17, 22.87, 22.63; HRMS m/z for $C_{55}H_{67}N_{12}O_8$ [M+H]$^+$, calcd 1023.5199, found 1023.5163).

Example 9

Conformational Analysis

Molecular mechanics and ab initio calculations were used to predict the conformations of oligomers produced as described in Examples 1-8, and the predictions confirmed by 2D NMR analysis. Molecular mechanics studies were performed with Macromodel (MMFF force field in chloroform) and ab initio calculations were conducted with the Gaussian 03 program package (DFT B3LYP method at 6-31 G* level).

First, the conformational preferences of triazole dimer 5 was calculated, which, as shown in FIGS. 2A-D, can adopt two anti and two syn conformations. The syn and anti conformations are defined based on the relative direction of the dipoles in adjacent rings. Both molecular mechanics and ab initio studies predict that the anti conformations are ~4 Kcal/mol more stable than the syn conformations. The limitation imposed by the anti conformation on the possible number of rotamers was expected to lead to a specific set of defined backbone structures.

Figure 5:
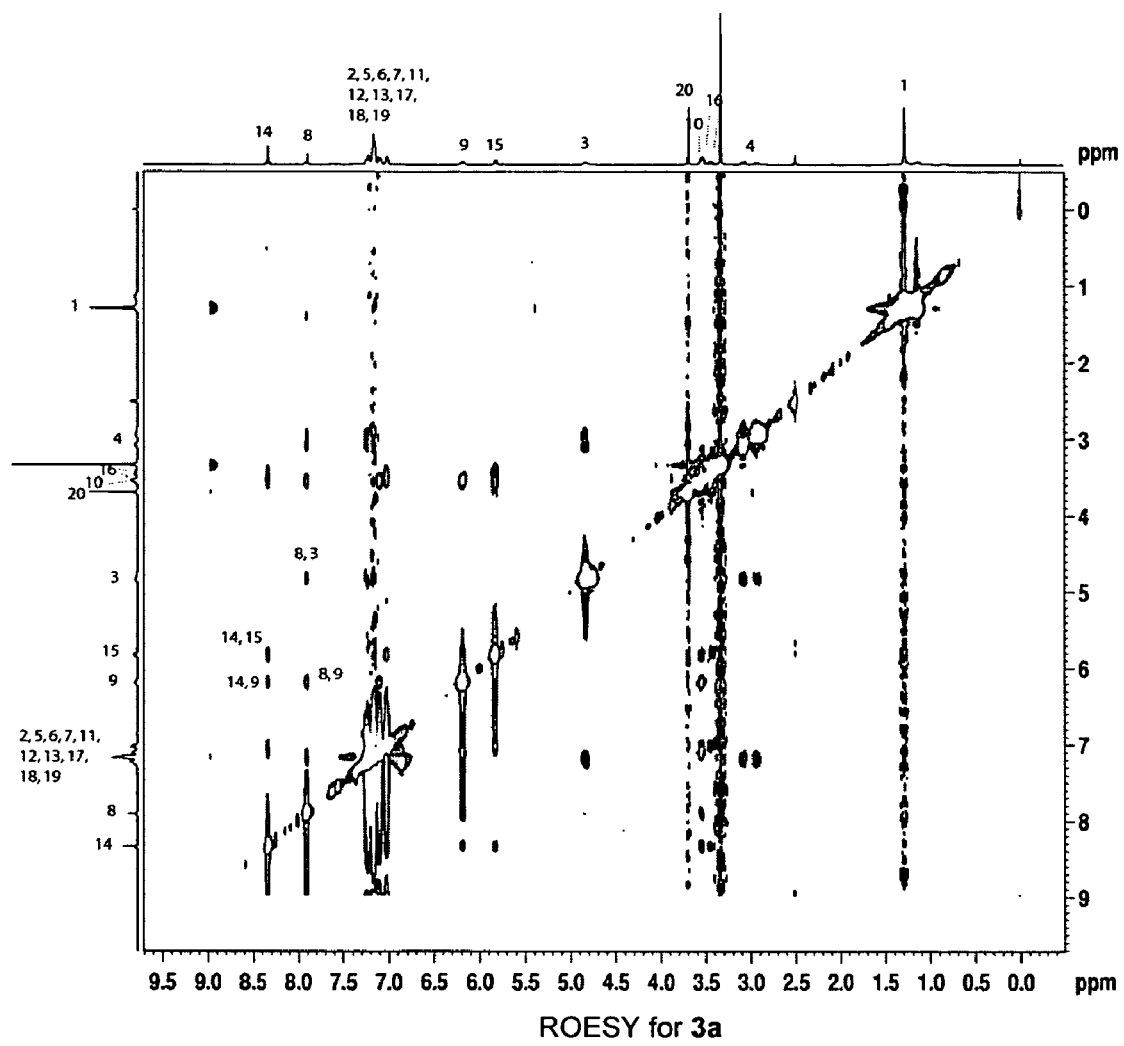
Figure 6:
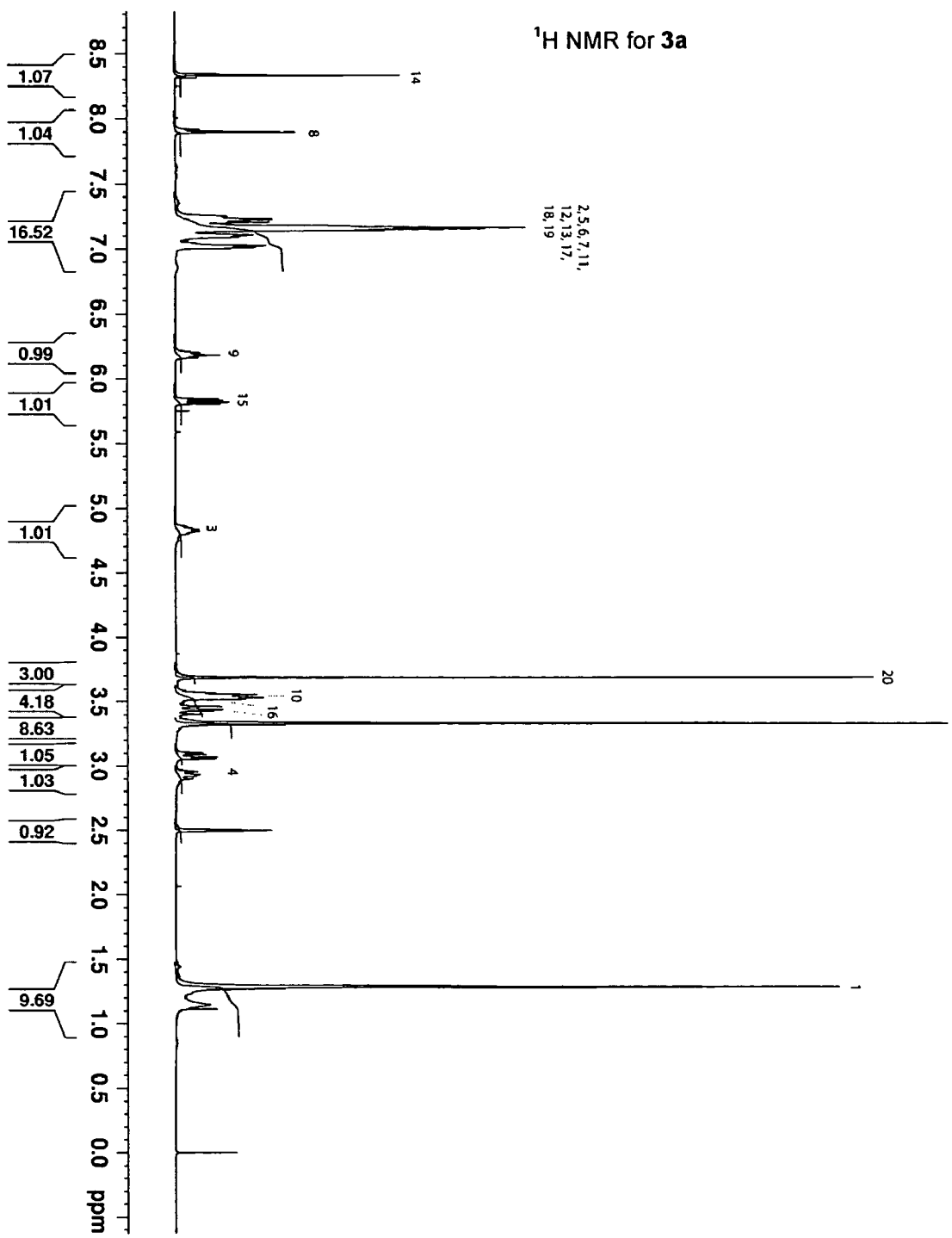
Figure 7:
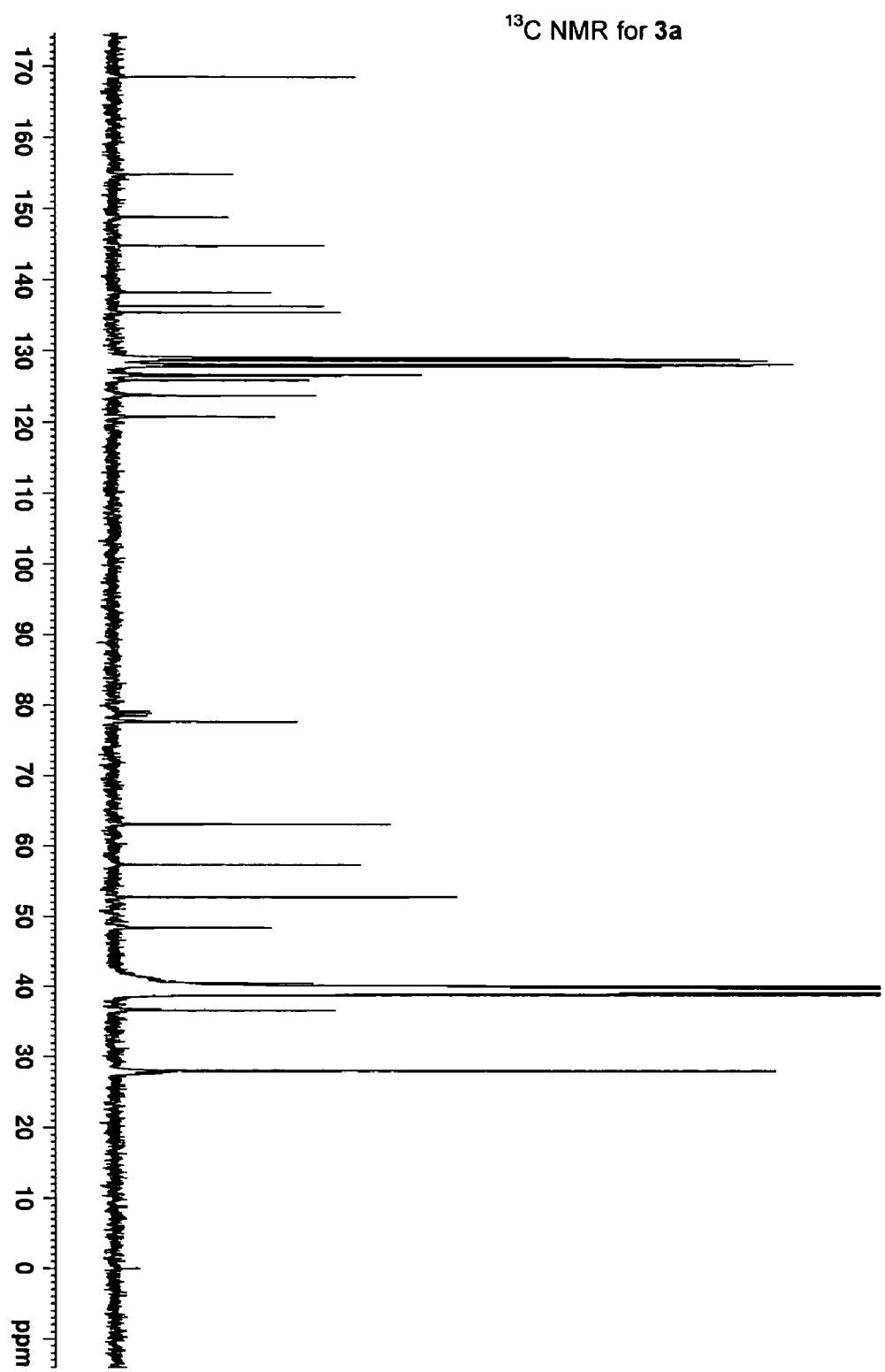
Figure 9:
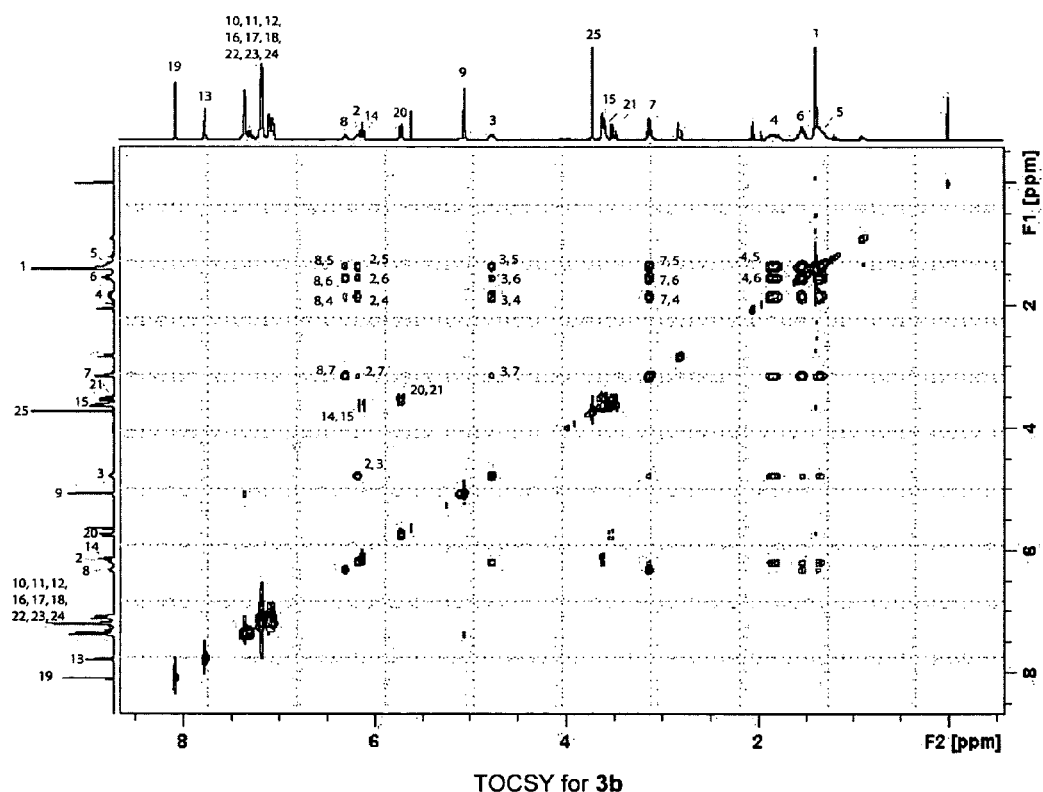
FIG. 9 is an image of the TOCSY spectrum for triazolamer 3b.
Figure 10:
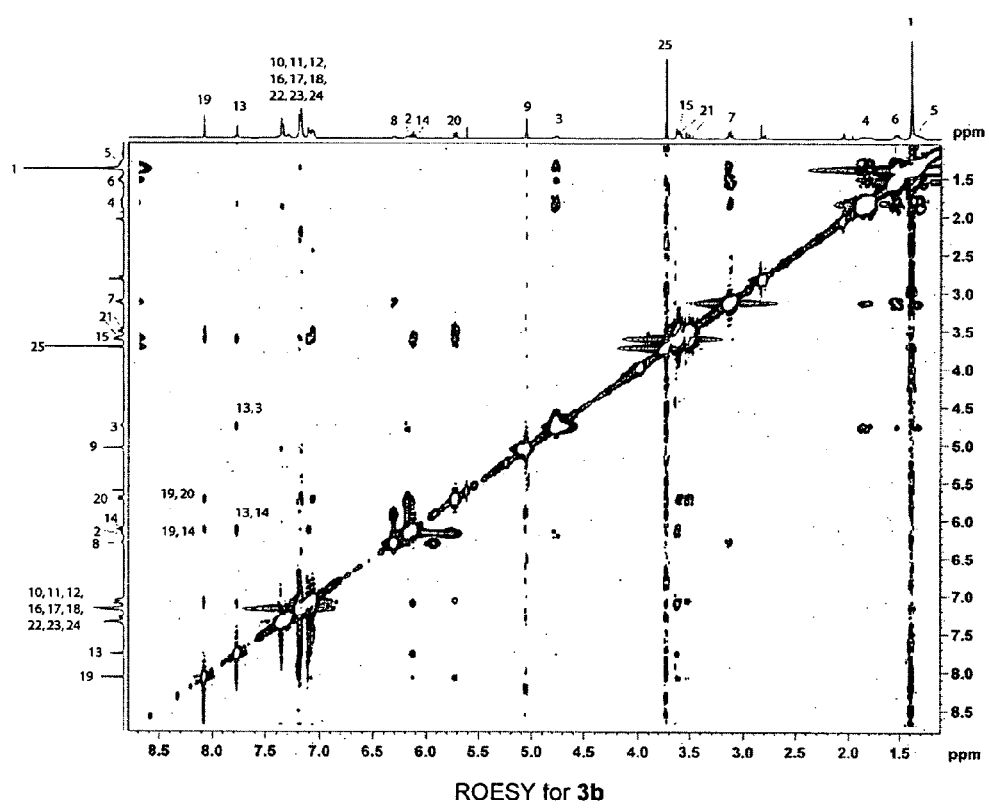
FIG. 10 is an image of the ROESY spectrum for triazolamer 3b.
Figure 11:
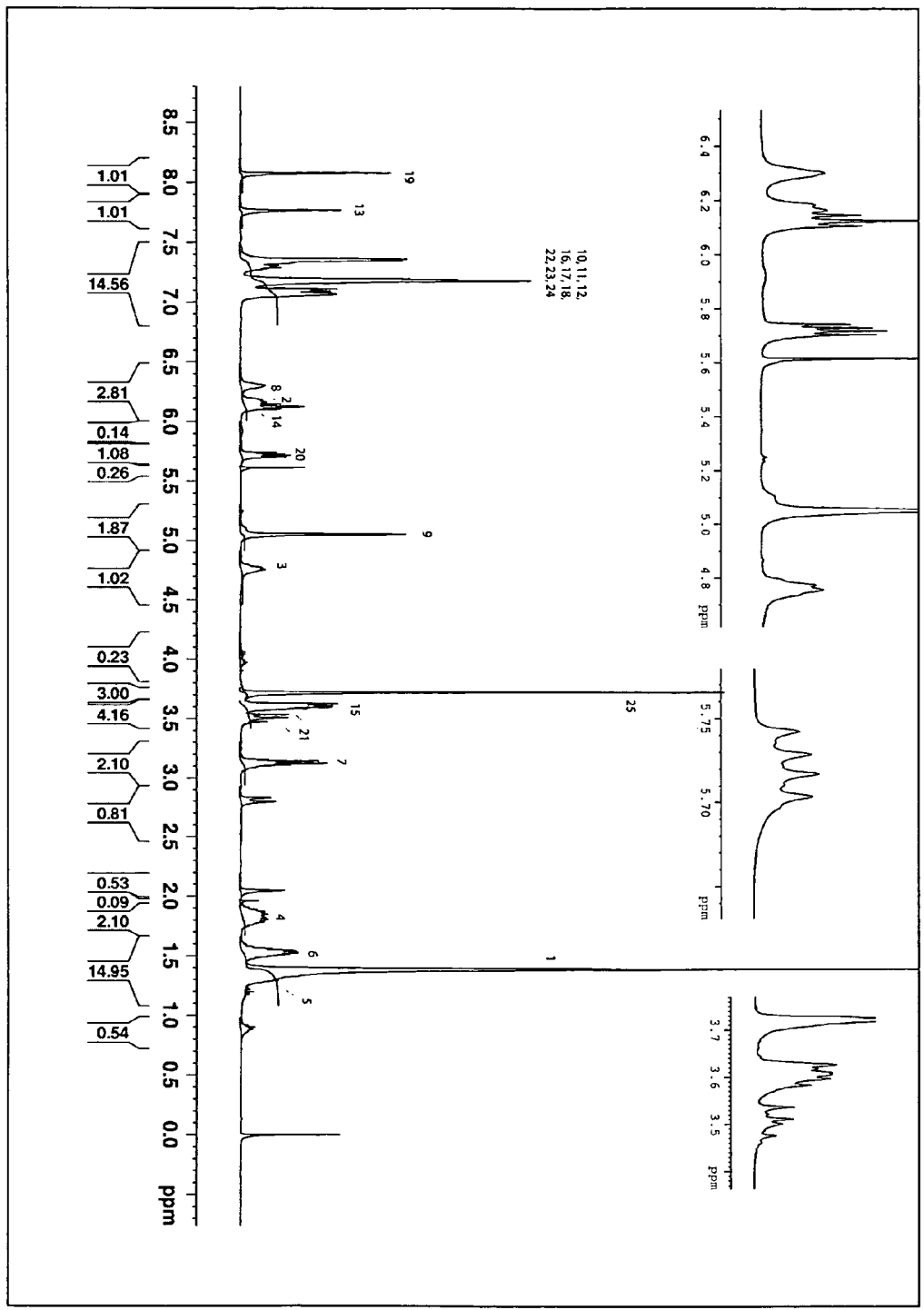
FIG. 11 is an image of the $^1$H NMR spectrum for triazolamer 3b.
Figure 12:
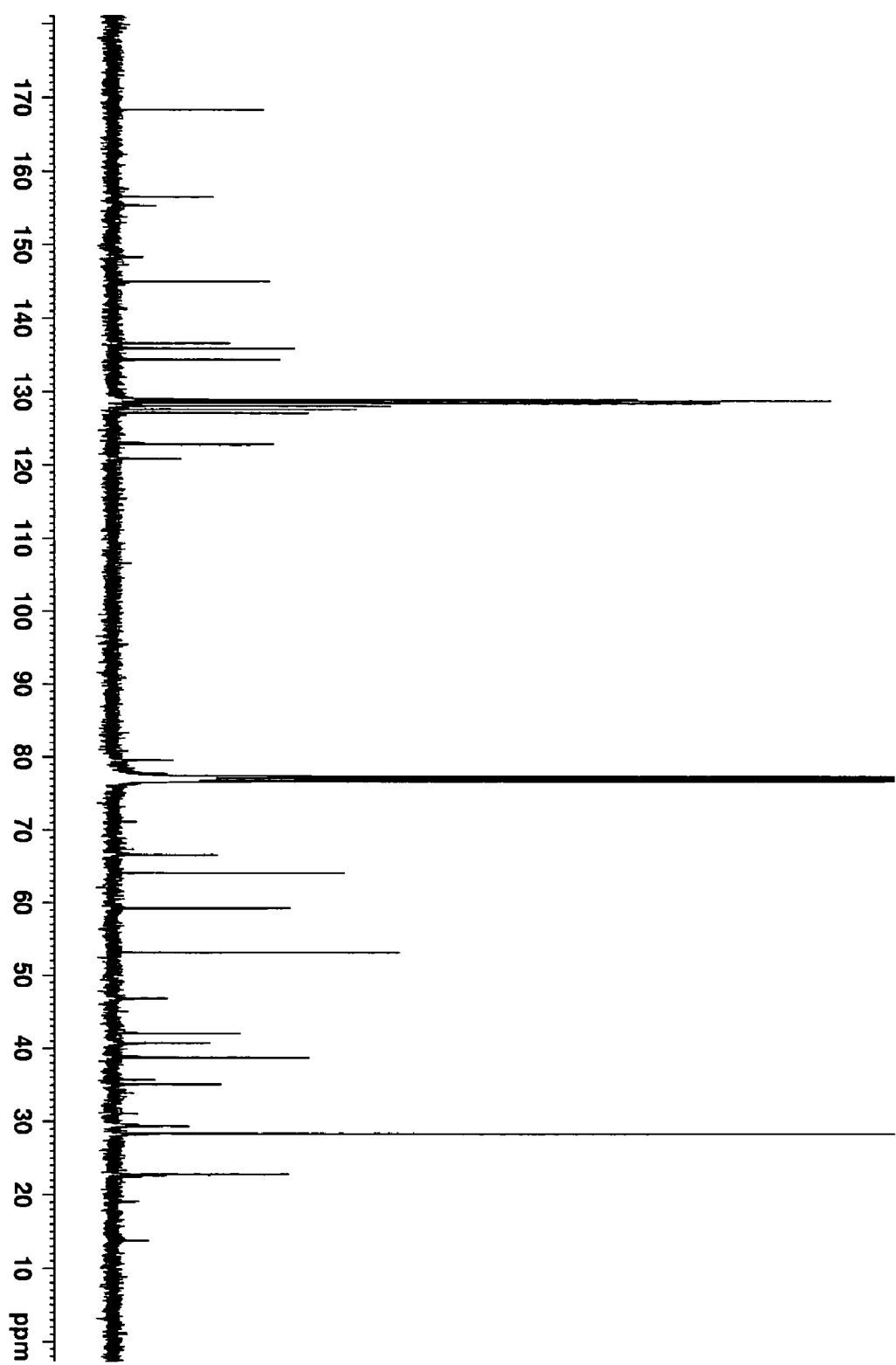
FIG. 12 is an image of the $^{13}$C NMR spectrum for triazolamer 3b.
Figure 14:
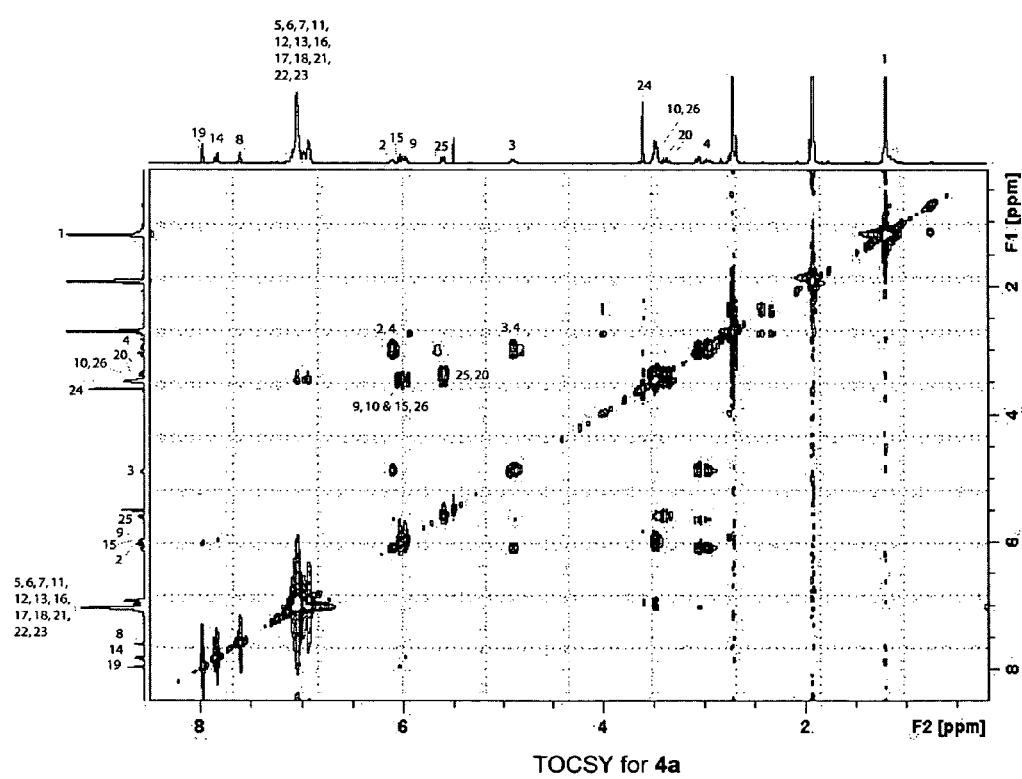
Figure 15:
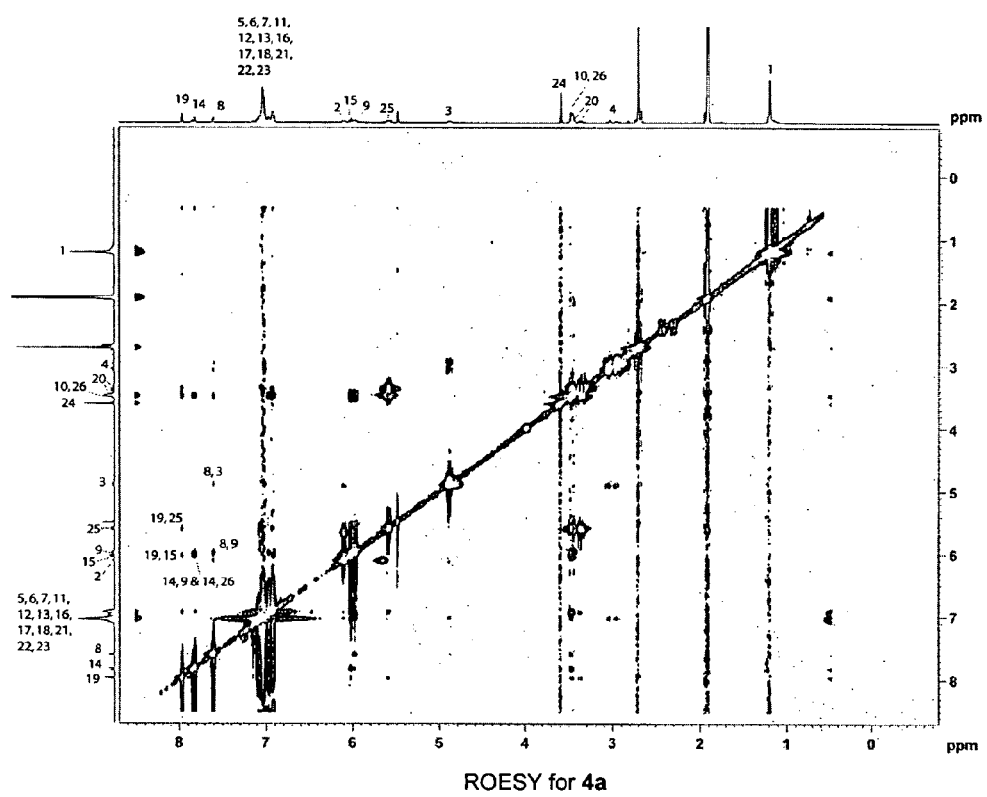
Figure 16:
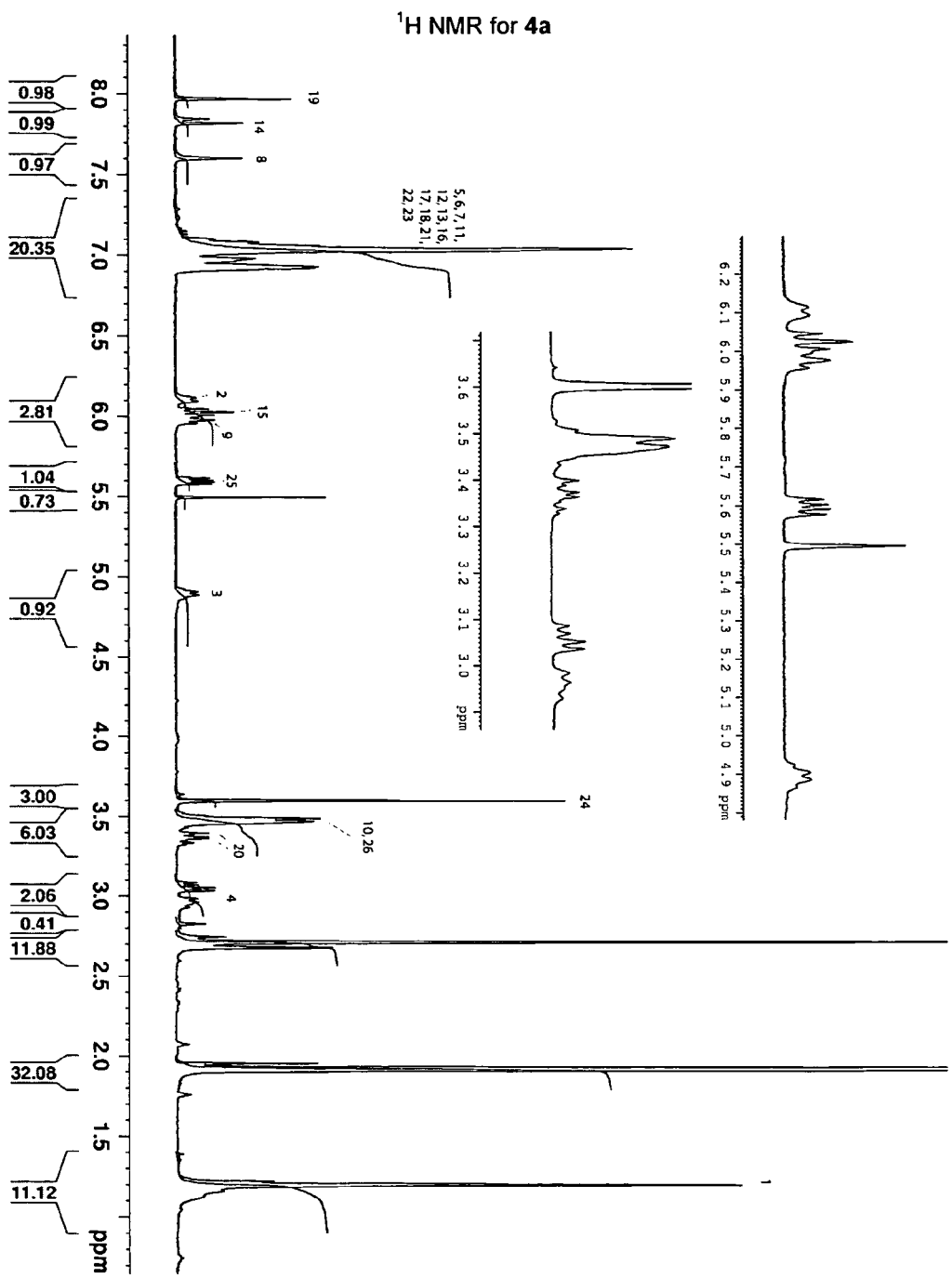
Figure 17:
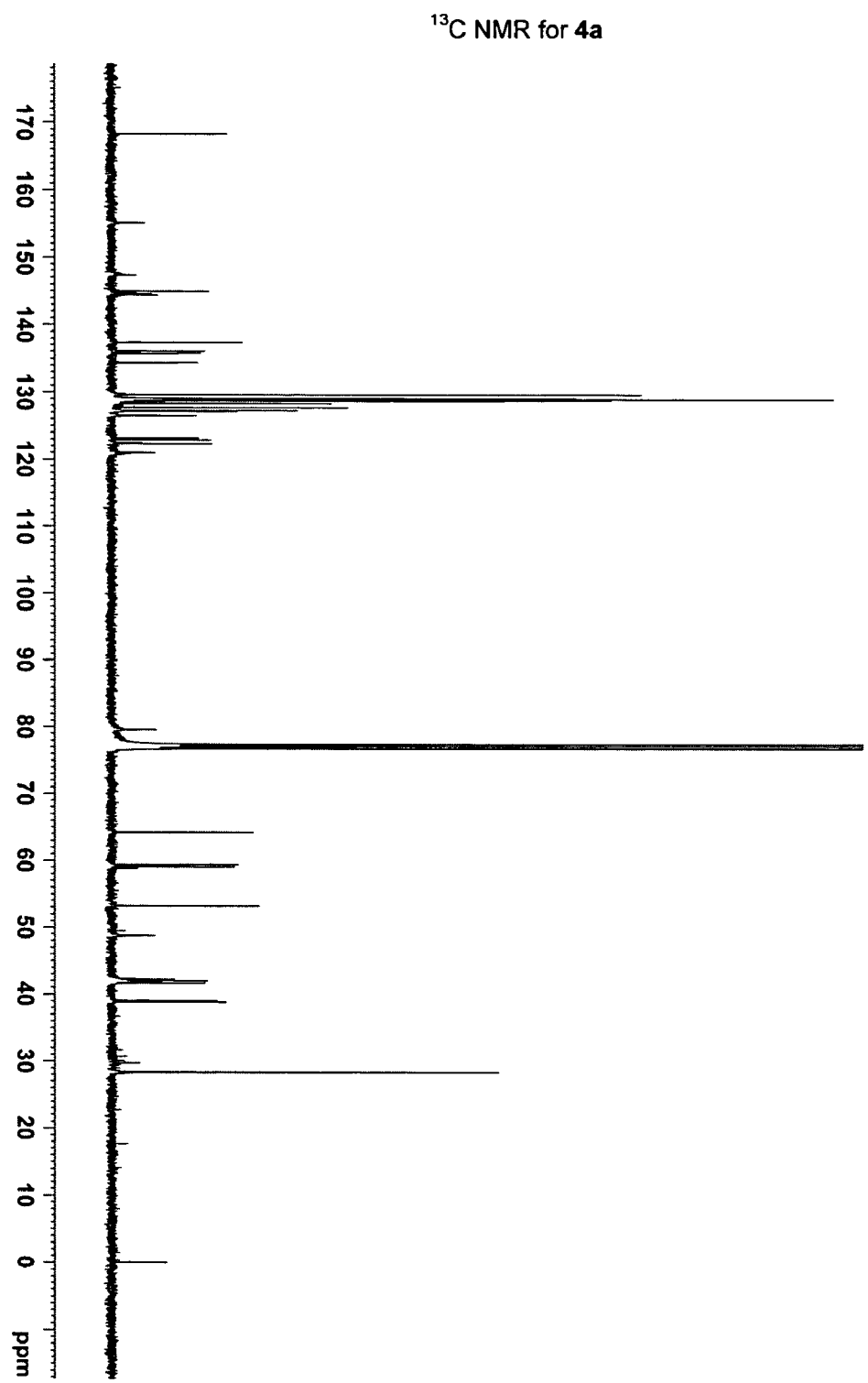
Figure 18:
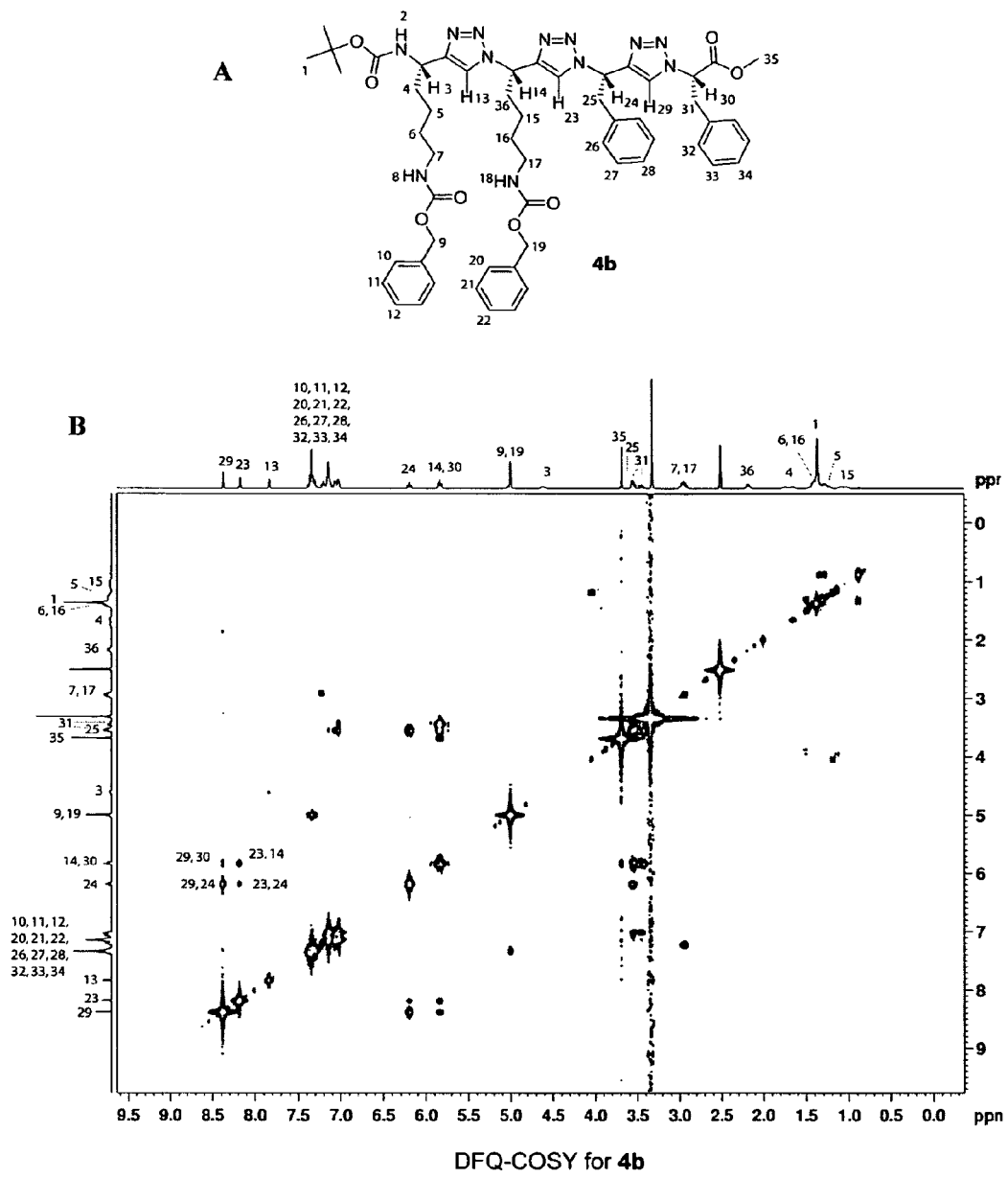
FIGS. 18A-B are a schematic diagram of triazolamer 4b (FIG. 18A) and an image of its DFQ-COSY spectrum (FIG. 18B).
Figure 19:
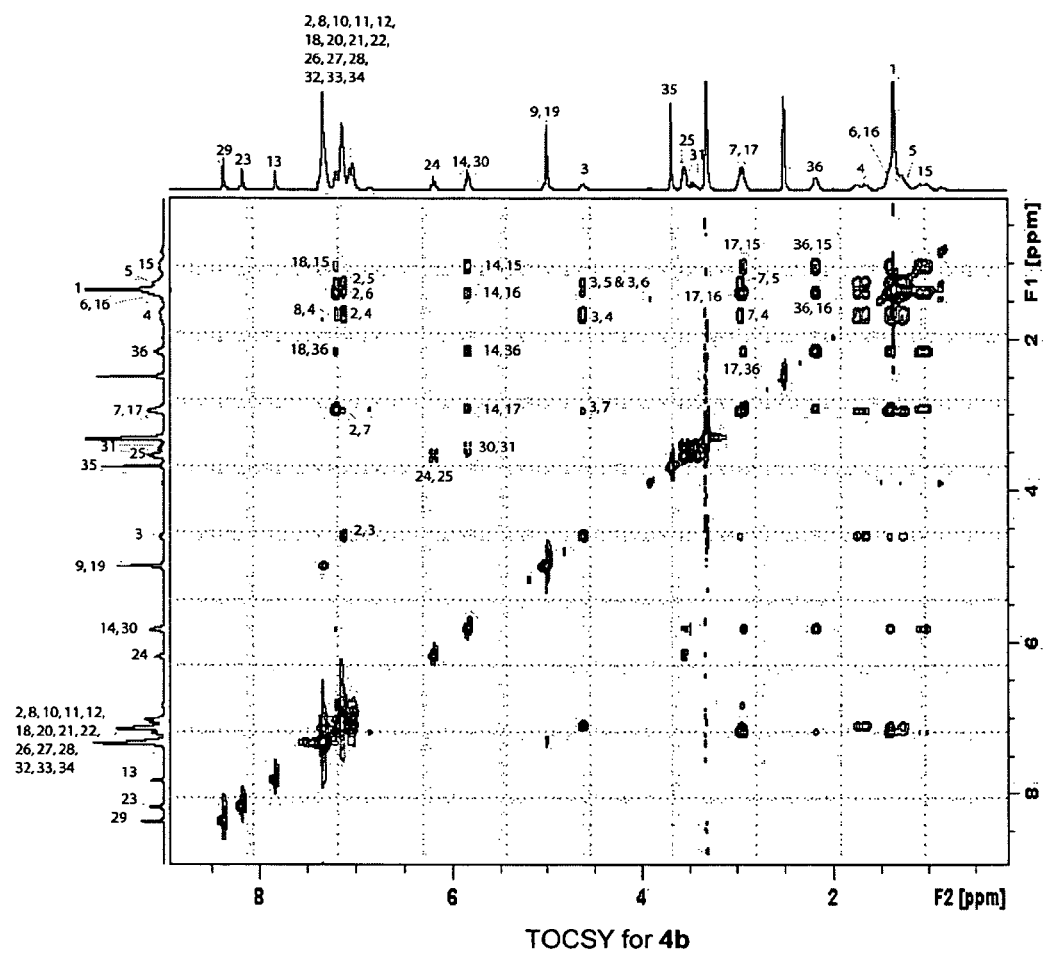
FIG. 19 is an image of the TOCSY spectrum for triazolamer 4b.
Figure 20:
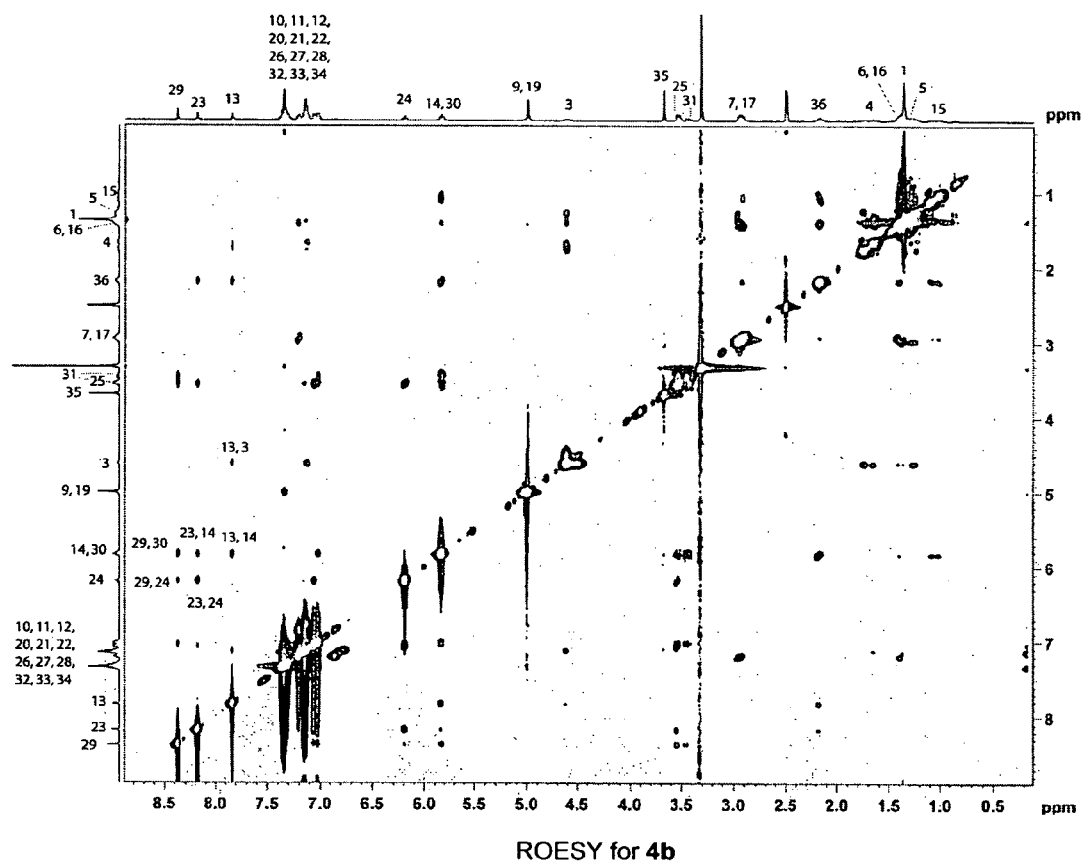
FIG. 20 is an image of the ROESY spectrum for triazolamer 4b.
Figure 21:
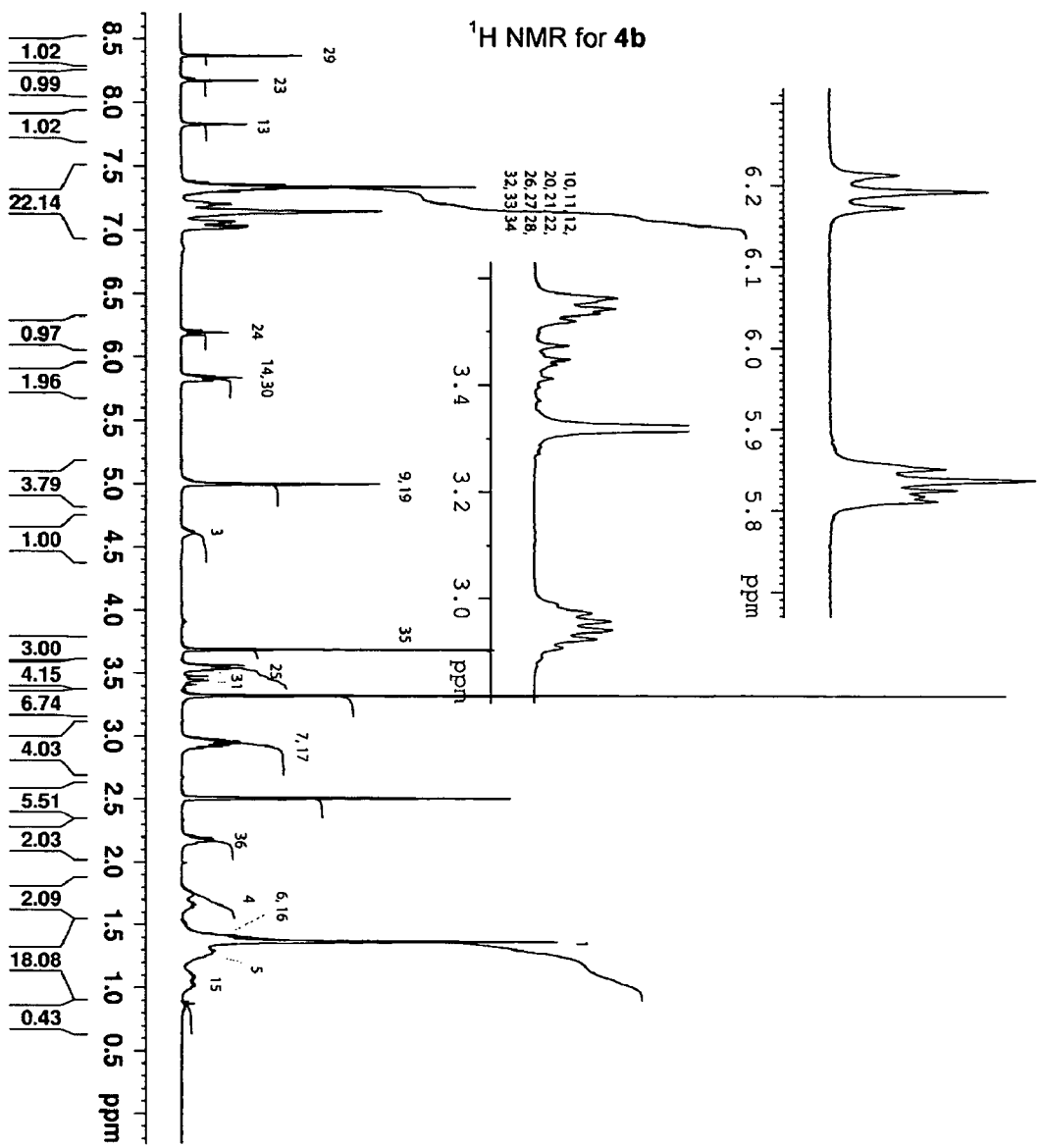
FIG. 21 is an image of the $^1$H NMR spectrum for triazolamer 4b.
Figure 22:
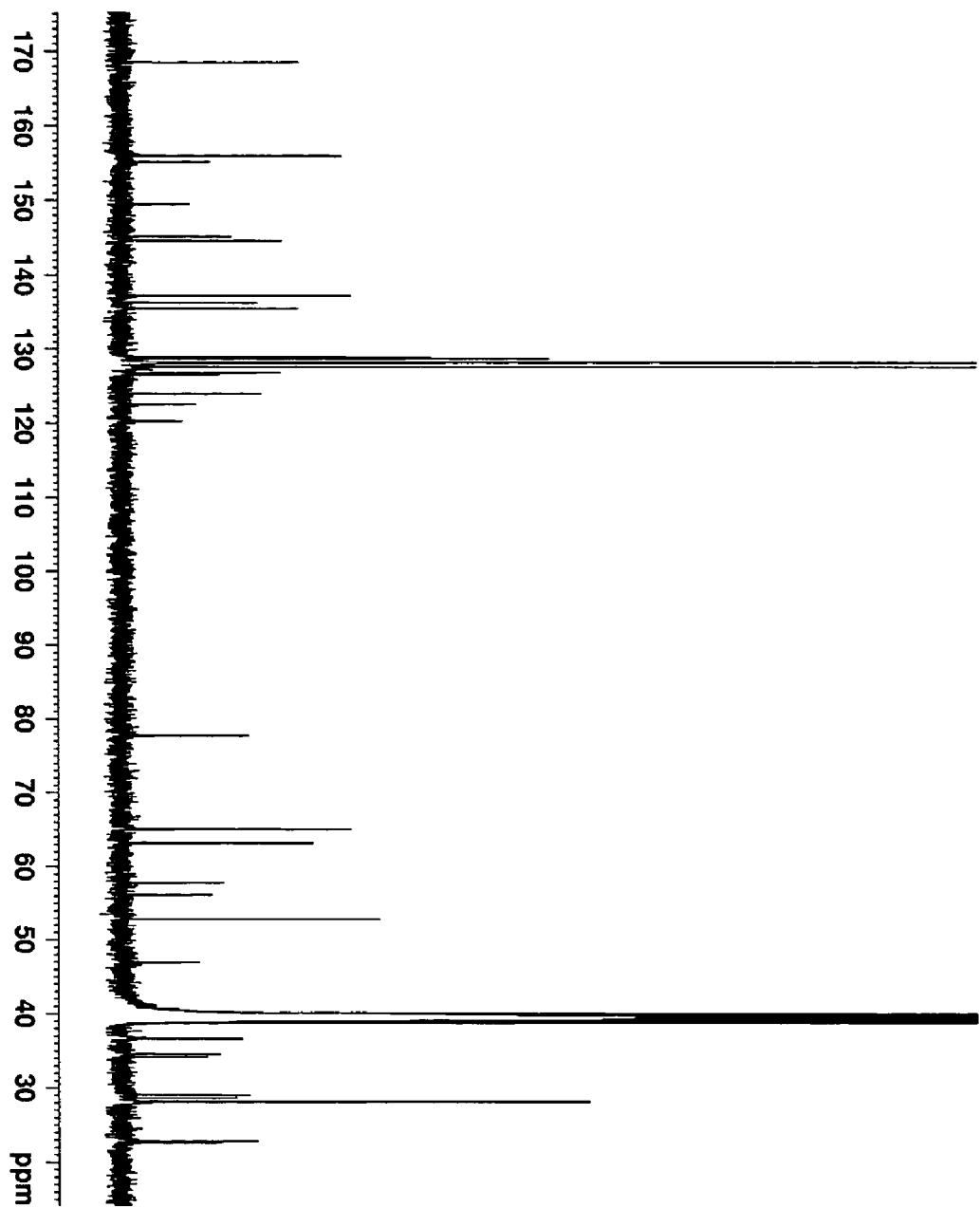
FIG. 22 is an image of the $^{13}$C NMR spectrum for triazolamer 4b.

NMR studies were performed on triazolamers 3a (FIGS. 3A-B and FIGS. 4-7), 3b (FIGS. 8A-B and FIGS. 9-12), 4a (FIGS. 13A-B and FIGS. 14-17), and 4b (FIGS. 18A-B, FIGS. 19-22, and FIGS. 23A-B). Examination of the 2D NMR spectra reveals that the backbones of triazolamers 3 and 4 predominantly adopt zigzag structures representing the anti conformation, as illustrated FIGS. 24A-B (see FIGS. 27A-D). NMR studies were performed in acetone-$d_6$ or DMSO-$d_6$ solutions, because the aromatic proteins were well dispersed in these solvents. A combination of TOCSY, DFQ-COSY, and ROESY experiments was used to assign $^1$H NMR resonances. It has been confirmed that triazolamer 4b retains its structure in methanol.

The preference for anti over syn can be rationalized by considering the dipole-dipole interactions between the two neighboring triazole rings, shown in FIG. 25. The 1,2,3-triazole ring features a large dipole (~5 Debye) that bisects the ring plane near atoms N3 and C5.

FIGS. 26A-D illustrate the predicted backbone conformations for the tetramer series. As the number of rings increases, the oligomer may adopt two backbone conformations while retaining the anti geometry between adjacent triazole rings. Analysis of the ROESY spectra of the tetramers suggests that the zigzag backbone conformation (FIG. 26B) is favored over the turn conformation (FIG. 26A). The major conformation of each compound is readily revealed by the intensity of ROE crosspeaks between the triazole ring protons and the adjoining $C_\alpha$ protons, as shown in FIGS. 26C-D. The turn conformations would be expected to provide near-equal intensity ROE crosspeaks between the triazole ring protons (proton c in FIG. 26C) and the adjoining $C_\alpha$ protons (protons b and d in FIG. 26C), because the distances between protons b-c and c-d are predicted to be similar (2.8 Å) in the turn conformation. Alternatively, in the zigzag conformation, the pattern and intensities of ROE crosspeaks between the same set of ring protons are expected to be substantially different, as the distances between b'-c' and c'-d' protons in the zigzag conformation are 2.8 Å and 3.9 Å, respectively (FIG. 26D). Examination of the 2D NMR spectra reveals that the backbones of triazolamers 3 and 4 predominantly adopt zigzag conformations in solution, as illustrated in FIGS. 27A-D. It remains to be determined what specific backbone structure will predominate in longer oligomers or in compounds with different side chain groups.

The zigzag triazolamer structure is reminiscent of peptide β-strand conformation (see FIG. 24B) and oligopyrrolinones described by Smith and Hirschmann (Smith et al., *Bioorg. Med. Chem.* 7:9-22 (1999); Smith et al., *J. Med. Chem.* 37:215-218 (1994), which are hereby incorporated by reference in their entirety). The axial distance between i and i+2 residues in β-strands is 7.2 Å; this distance is roughly 7.9 Å in the zigzag-triazolamer. The $C_\beta$ to $C_\beta$ distances in adjacent residues is 5.5 Å in β-strands and a little longer (6.8 Å) in the triazolamer. Thus, one surface of the zigzag-triazolamer may effectively mimic a β-strand and prove useful for targeting protein pockets and surfaces involved in β-strand recognition (Loughlin et al., *Chem. Rev.* 104:6085-6117 (2004), which is hereby incorporated by reference in its entirety). Although the triazolamer backbone does not offer a β-strand's hydrogen bond functionality, the N-2 and N-3 electron pairs may serve as hydrogen bond acceptors (Brik et al., *ChemBioChem* 6:1167-1169 (2005), which is hereby incorporated by reference in its entirety). These triazolamers are β-strand mimetics that display chiral side chains and preserve extended conformation.

In summary, an approach for the synthesis of nonpeptidic scaffolds capable of displaying protein-like side chains by swapping amide bonds with 1,2,3-triazole rings is disclosed herein. The overall conformation of these triazole oligomers appears to be dictated by dipole-dipole interactions between adjacent rings. Solution NMR studies suggest that a zigzag conformation, which closely mimics the β-strand structure, predominates in two different tetramers.

Example 10

1,3-Substituted Triazolamers as a General Class of Protease Inhibitors

To determine whether 1,3-triazolamers of the present invention can selectively inhibit the activity of target proteases, inhibition is being tested with the HIV-1 protease as a model (Brik et al., "1,2,3-Triazole as a Peptide Surrogate in the Rapid Synthesis of HIV-1 Protease Inhibitors," *ChemBiochem* 6:1167-9 (2005), which is hereby incorporated by reference in its entirety). HIV-1 was chosen as the initial target because of the plethora of ligand-bound protease structures in the Protein Data Bank and the availability of well-established assays for inhibition studies.

FIGS. 28A-B show two well-studied HIV-1 protease inhibitors that inhibit the protease with very high affinities: L-700,417 (Bone et al., "X-Ray Crystal-Structure of the HIV Protease Complex with L-700,417, an Inhibitor with Pseudo C2 Symmetry," *J. Am. Chem. Soc.* 113:9382-4 (1991), which is hereby incorporated by reference in its entirety) (FIG. 28A) and A-74704 (Erickson et al., "Design, Activity, and 2.8 Å Crystal Structure of a C2 Symmetric Inhibitor Complexed to HIV-1 Protease," *Science* 249:521-33 (1990), which is hereby incorporated by reference in its entirety) (FIG. 28B). Importantly, both inhibitors have been crystallized in complex with HIV-1, allowing these "tetrapeptides," which feature bulky hydrophobic side chains, to be used to design triazolamers as potential inhibitors of HIV-1. Triazolamers 8-10 (FIGS. 28C-E) were chosen for initial studies, because modeling suggested that these triazolamers superimpose well with the inhibitors in their protein-bound conformations, as shown in FIGS. 29A-E. FRET-based assays are currently being utilized to determine the efficacy of these triazolamers as HIV-1 protease inhibitors (Matayoshi et al., "Novel Fluorogenic Substrates for Assaying Retroviral Proteases by Resonance Energy Transfer," *Science* 247:954-8 (1990), which is hereby incorporated by reference in its entirety). If these compounds perform well in this assay, the ability of triazolamers to inhibit HIV-1 infection in cell culture will be tested. It is expected that triazolamers 8-10 will inhibit HIV-1 infection in culture to a similar degree as their known protease inhibitor counterparts.

The methods of the present invention contemplate the design of non-peptidic oligomers with favorable cell uptake properties. These cell-based studies will also allow the cell-permeability of these triazolamers to be tested. Moreover, this HIV-1-related assays will provide important insights into the behavior of triazolamers as specific ligands for protein pockets that recognize β-strand motifs, and the information gleamed from these studies will be utilized to target other important proteases and protein-protein interactions (Loughin et al, "Beta-Strand Mimetics," *Chem. Rev.* 104: 6085-117 (2004); Tyndall et al., "Proteases Universally Recognize Beta Strands in Their Active Sites," *Chem. Rev.* 105: 973-99 (2005), which are hereby incorporated by reference in their entirety).

Example 11

Helices from 1,3-Triazolamers

The present invention affords a diverse range of oligomers that adopt defined conformations, including nonpeptidic helical structures that display protein-like functionality. It was predicted that helical conformations could be obtained by capturing successive turn conformations in triazolamers. Modeling suggests that the lowest energy turn in a triazolamer helix contains four residues with a pitch of 5.4 Å, as shown in FIGS. 30A-B. Based on modeling studies, it is expected that a hexamer would equilibrate between different zigzag and turn conformations, but that the desired helical turn could be populated by crosslinking the i and i+4 side chains, as often demonstrated with synthetic α-helices, as shown in FIGS. 30C-D (Andrews & Tabor, "Forming Stable Helical Peptides Using Natural and Artificial Amino Acids," *Tetrahedron* 55:11711-43 (1999), which is hereby incorporated by reference in its entirety). The constrained helical structures will be fully characterized by 2D NMR and CD spectroscopies.

The methods of the present invention provide ways to introduce drug-like functionality into nonpeptidic oligomers that maintain peptide chiral main-chain and amino acid side chains, can be produced from any amino acids, can adopt stable structural organizations even at very short lengths, and can be organized into non-natural peptides resistant to proteolytic degradation.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An oligomer of Formula I:

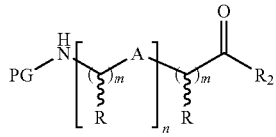

wherein each "A" moiety is independently a moiety of formula

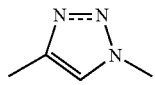

wherein ---- is a single or double bond;
PG is a protecting group suitable for protection of a terminal amine group;
each R is independently an amino acid side chain;
$R_2$ is $OR_3$ or $N(R_3)_2$, wherein $R_3$ is independently hydrogen, an alkyl group, or an aryl group;
~~~ is a single bond of undefined stereochemistry;
m is independently 1 or 2; and
n is two or any number greater than two.

2. The oligomer according to claim 1, wherein n is any number from 2 through 8.

3. The oligomer according to claim 1, wherein the protecting group is selected from the group consisting of tert-butyloxycarbonyl ("Boc"), 9-fluorenylmethyloxycarbonyl ("Fmoc"), carbobenzyloxy ("Cbz"), and trityl.

4. The oligomer according to claim 1, wherein $R_3$ is a $C_1$-$C_4$ alkyl.

5. The oligomer according to claim 4, wherein $R_3$ is methyl, ethyl, allyl, or t-butyl.

6. The oligomer according to claim 1, wherein $R_3$ is an aryl group selected from the group consisting of phenyl or benzyl.

7. The oligomer according to claim 1, wherein the oligomer comprises a conformation selected from the group consisting of a beta-strand, an α-helix, and a zigzag conformation.

8. The oligomer according to claim 1, wherein the oligomer is a protein inhibitor.

9. The oligomer according to claim 8, wherein the oligomer comprises a beta-strand conformation.

10. The oligomer according to claim 8, wherein the oligomer is selected from the group consisting of:

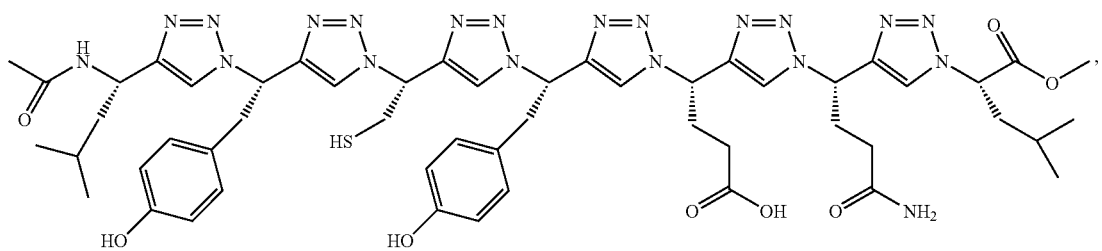

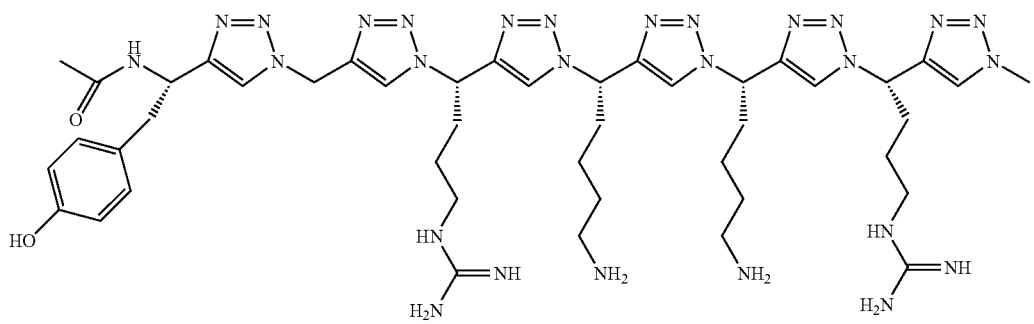

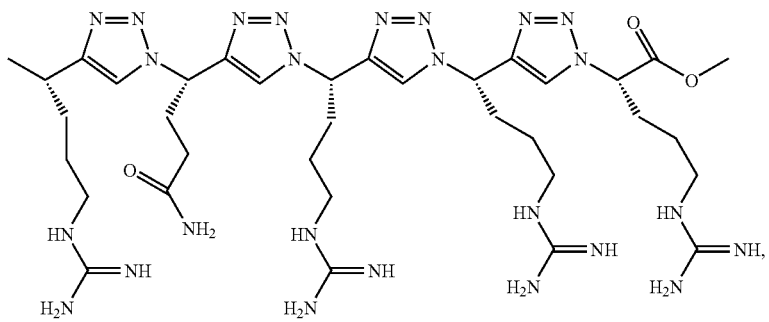

-continued
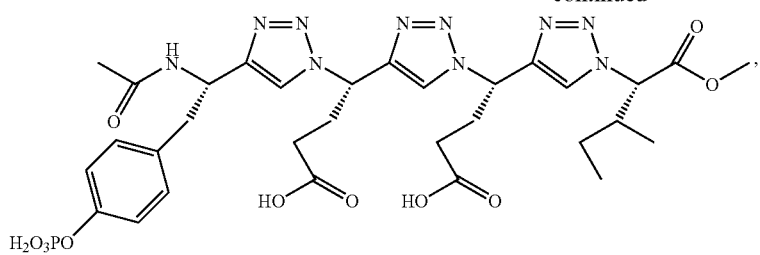
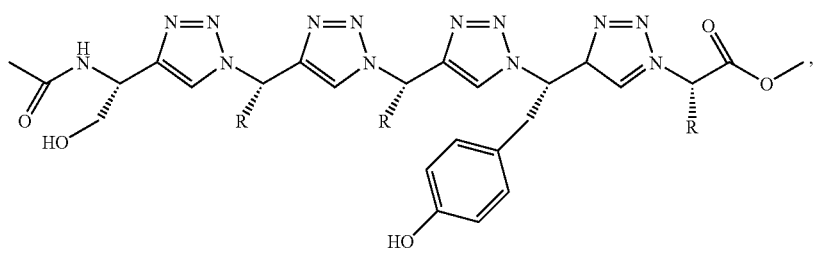
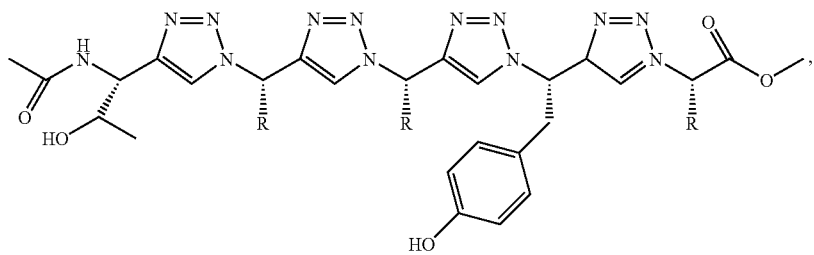
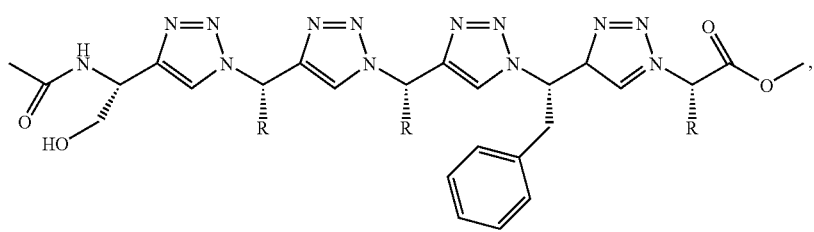
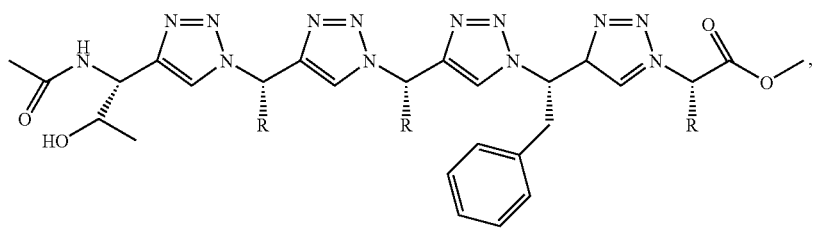
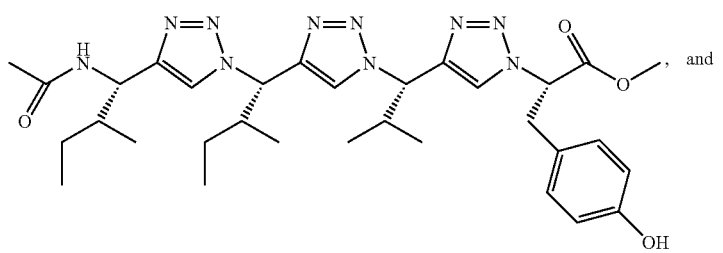

-continued

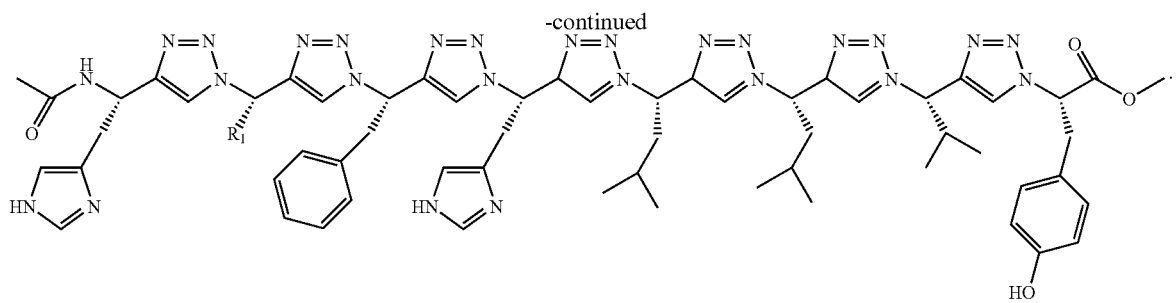

11. The oligomer according to claim 8, wherein the oligomer mimics the conformation of (i) a beta-strand of a protein selected from the group consisting of human papillomavirus E7 oncoprotein, HIV-1 Tat protein, and peptides containing the pYEEI sequence, or (ii) a protease inhibitor selected from the group consisting of A-74704, Ac-Leu-Phe-CF$_3$, Calpsin-Inhibitor I, and CGP 38'560.

12. The oligomer according to claim 8, wherein the oligomer interacts with a protease selected from the group consisting of HIV-1 Protease, chymotrypsin, 20S Proteasome, and renin.

13. An oligomer of Formula VII:

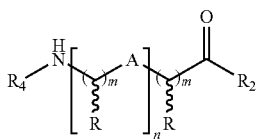

VII wherein each "A" moiety is independently a moiety of formula

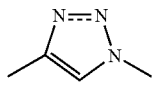

wherein ----- is a single or double bond;

R$_4$ is H or an alkanoyl;

each R is independently an amino acid side chain;

R$_2$ is OR$_3$ or N(R$_3$)$_2$, wherein R$_3$ is independently hydrogen, an alkyl group, or an aryl group;

∿∿ is a single bond of undefined stereochemistry;

m is independently 1 or 2; and n is two or any number greater than two.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: Natural substrate sequence recognized by 20S
      proteasome

<400> SEQUENCE: 1

Leu Leu Val Tyr
1

<210> SEQ ID NO 2
<211> LENGTH: 8
<212> TYPE: PRT
<213> ORGANISM: Artificial
<220> FEATURE:
<223> OTHER INFORMATION: Natural substrate sequence recognized by Renin
<220> FEATURE:
<221> NAME/KEY: UNSURE
<222> LOCATION: (2)..(2)
<223> OTHER INFORMATION: Xaa at position 2 is any amino acid

<400> SEQUENCE: 2

His Xaa Phe His Leu Leu Val Tyr
1               5

<210> SEQ ID NO 3
<211> LENGTH: 4
<212> TYPE: PRT
<213> ORGANISM: Artificial
<220> FEATURE:
<223> OTHER INFORMATION: Active site of protease inhibitor A-74704

<400> SEQUENCE: 3

Val Phe Phe Val
1
```